(12) United States Patent
Thompson et al.

(10) Patent No.: US 9,447,107 B2
(45) Date of Patent: Sep. 20, 2016

(54) BROADLY ABSORBING METALLOPORPHYRIN-BASED MULTICHROMOPHORIC ARRAYS FOR TRIPLET HARVESTING

(75) Inventors: Mark E. Thompson, Anaheim, CA (US); Matthew T. Whited, Northfield, MN (US); Peter I. Djurovich, Long Beach, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/229,477

(22) Filed: Sep. 9, 2011

(65) Prior Publication Data

US 2012/0168697 A1 Jul. 5, 2012

Related U.S. Application Data

(60) Provisional application No. 61/381,819, filed on Sep. 10, 2010, provisional application No. 61/392,457, filed on Oct. 12, 2010.

(51) Int. Cl.
| | | |
|---|---|---|
| *G02B 5/20* | (2006.01) | |
| *C07D 487/22* | (2006.01) | |
| *C09B 47/04* | (2006.01) | |
| *C09K 9/02* | (2006.01) | |

(Continued)

(52) U.S. Cl.
CPC ........... *C07D 487/22* (2013.01); *C09B 47/045* (2013.01); *C09B 47/073* (2013.01); *C09B 57/10* (2013.01); *C09K 9/02* (2013.01); *C09K 11/06* (2013.01); *H01L 51/009* (2013.01); *C09K 2211/1029* (2013.01); *C09K 2211/1055* (2013.01); *C09K 2211/185* (2013.01); *H01L 51/008* (2013.01); *H01L 51/0087* (2013.01); *Y02E 10/549* (2013.01)

(58) Field of Classification Search
USPC ........... 252/586; 427/74, 337, 340; 540/145; 257/40, E51.026; 438/82
See application file for complete search history.

(56) References Cited

U.S. PATENT DOCUMENTS 6,004,530 A 12/1999 Sagner et al.

FOREIGN PATENT DOCUMENTS

| EP | 1 311 141 A1 | 5/2003 |
|---|---|---|
| EP | 2 230 242 A1 | 9/2010 |
| WO | WO 98/03865 | 1/1998 |

OTHER PUBLICATIONS

E. Maligaspe, T. Kumpulainen, N. K. Subbaiyan, M. E. Zandler, H. Lemmetyinen, N. V. Tkachenko and F. D'Souz Electronic energy harvesting multi BODIPY-zinc porphyrin dyads accommodating fullerene as photosynthetic composite of antenna-reaction center, Phys. Chem. Chem. Phys., 2010, 12, 7434-7444.*

(Continued)

*Primary Examiner* — Bijan Ahvazi
(74) *Attorney, Agent, or Firm* — Finnnegan, Henderson, Farabow, Garrett & Dunner, L.L.P.

(57) ABSTRACT

The present disclosure relates to multichromophoric assemblies comprising metalloporphyrin scaffolds. The present disclosure also relates, in part, to methods for generating electric-field-stabilized geminate polaron pairs comprising applying electric fields to the multichromophoric assemblies described herein, or alternatively, directly to the metalloporphyrins provided by the present disclosure. The present disclosure further relates, in part, to multichromophoric assemblies comprising metalloporphyrin scaffolds, which exhibit enhanced energy transfer properties.

13 Claims, 15 Drawing Sheets

(51) Int. Cl.
*C09K 11/06* (2006.01)
*C09B 47/073* (2006.01)
*C09B 57/10* (2006.01)
*C07B 47/00* (2006.01)
*H01L 51/00* (2006.01)

(56) References Cited

OTHER PUBLICATIONS

Vadim Adamovich, Jason Brooks, Arnold Tamayo, Alex M. Alexander, Peter I. Djurovich, Brian W. D'Andrade, Chihaya Adachi, Stephen R. Forrest and Mark E. Thompson, High efficiency single dopant white electrophosphorescent light emitting diodes,New J. Chem., 2002, 26, 1171-1178.*
Carsten Borek, Kenneth Hanson, Peter I. Djurovich, Mark E. Thompson, Kristen Aznavour,Robert Bau, Yiru Sun, Stephen R. Forrest, Jason Brooks, Lech Michalski, and Julie Brown, Highly Efficient, Near-Infrared Electrophosphorescence from a Pt-Metalloporphyrin Complex,Angew. Chem. Int. Ed. 2007, 46, 1109-1112.*
Wu, Wenting, et al., "The Synthesis of 5,10,15,20-tetraarylporphyrins and their Platinum (II) Complexes as Luminescent Oxygen Sensing Materials", Dyes and Pigments, vol. 89 (2011) pp. 199-211.
Bedel-Cloutour, Catherine H., "Syntheses of Functionalized Indium Porphyrins for Monoclonal Antibody Labeling", Bioconjugate Chemistry, vol. 7, No. 6, Nov./Dec. 1996, pp. 617-627.
Esser, Peter E., et al., "Syntheses and Photochemistry of Fluorinated and Chlorinated Titanium Porphyrinates: Crystal Structure of Oxotitanium meso-Tetrakis (2,3,4,5,6-pentafluorophenyl) porphyrinate", Chem. Ber. , vol. 129, 1996, pp. 833-836.
Agarwal, Neeraj, "The Synthesis and Characterization of Photonic Materials Composed of Substituted Fluorene Donors" Dyes and Pigments, vol. 83 (2009) pp. 328-333.
Holmes-Smith, A.S., et al., "Characterization of an Electropolymerized Pt (II) Diamino Phenyl Porphyrin Polymer Suitable for Oxygen Sensing", Measurement Science and Technology, vol. 17 (2008) pp. 3328-3334.
Papkovsky, Dmitro B., et al., "Emerging Applications of Phosphorescent Metalloporphyrins", Journal of Fluorescence., vol. 15, No. 4, Jul. 2005, pp. 569-584.
Amao, Yutaka, et al., "Platinum Tetrakis (Pentafluorophenyl) Porphyrin Immobilized in Polytrifluoroethylmethacrylate Film as a Photostable Optical Oxygen Detection Material", Journal of Fluorine Chemistry, vol. 107 (2001) pp. 101-106.
Ziessel, Raymond, et al., "Boron Dipyrin Dyes Exhibiting "Push-Pull-Pull" Electronic Signatures" Chem., European Journal, vol. 15 (2009), pp. 10369-10376.

\* cited by examiner

BROADLY ABSORBING METALLOPORPHYRIN-BASED MULTICHROMOPHORIC ARRAYS FOR TRIPLET HARVESTING

CROSS-REFERENCE TO RELATED APPLICATIONS

This application claims the benefit of U.S. Provisional Application Nos. 61/381,819, filed Sep. 10, 2010, and 61/392,457, filed Oct. 12, 2010, the disclosure of which are incorporated herein by reference.

STATEMENT REGARDING FEDERALLY SPONSORED RESEARCH

The subject matter of this application was prepared with U.S. Government support under Grant No. DE-SC0001011 awarded by the Department of Energy. The government has certain rights in the subject matter of this application.

JOINT RESEARCH AGREEMENT

The subject matter of this application was made by, on behalf of, and/or in connection with one or more of the following parties to a joint university-corporation research agreement: University of Southern California and Global Photonic Energy Corporation. The agreement was in effect on and before the date the claimed invention was made, and the claimed invention was made as a result of activities undertaken within the scope of the agreement.

BACKGROUND

Optoelectronic devices rely on the optical and electronic properties of materials to either produce or detect electromagnetic radiation electronically or to generate electricity from ambient electromagnetic radiation.

Photosensitive optoelectronic devices convert electromagnetic radiation into electricity. Solar cells, also called photovoltaic (PV) devices, are a type of photosensitive optoelectronic device that is specifically used to generate electrical power. PV devices, which may generate electrical energy from light sources other than sunlight, can be used to drive power consuming loads to provide, for example, lighting, heating, or to power electronic circuitry or devices such as calculators, radios, computers or remote monitoring or communications equipment. These power generation applications also often involve the charging of batteries or other energy storage devices so that operation may continue when direct illumination from the sun or other light sources is not available, or to balance the power output of the PV device with a specific application's requirements. As used herein the term "resistive load" refers to any power consuming or storing circuit, device, equipment or system.

Another type of photosensitive optoelectronic device is a photoconductor cell. In this function, signal detection circuitry monitors the resistance of the device to detect changes due to the absorption of light.

Another type of photosensitive optoelectronic device is a photodetector. In operation a photodetector is used in conjunction with a current detecting circuit which measures the current generated when the photodetector is exposed to electromagnetic radiation and may have an applied bias voltage. A detecting circuit as described herein is capable of providing a bias voltage to a photodetector and measuring the electronic response of the photodetector to electromagnetic radiation.

These three classes of photosensitive optoelectronic devices may be characterized according to whether a rectifying junction as defined below is present and also according to whether the device is operated with an external applied voltage, also known as a bias or bias voltage. A photoconductor cell does not have a rectifying junction and is normally operated with a bias. A PV device has at least one rectifying junction and is operated with no bias. A photodetector has at least one rectifying junction and is usually but not always operated with a bias. As a general rule, a photovoltaic cell provides power to a circuit, device or equipment, but does not provide a signal or current to control detection circuitry, or the output of information from the detection circuitry. In contrast, a photodetector or photoconductor provides a signal or current to control detection circuitry, or the output of information from the detection circuitry but does not provide power to the circuitry, device or equipment.

Traditionally, photosensitive optoelectronic devices have been constructed of a number of inorganic semiconductors, e.g., crystalline, polycrystalline and amorphous silicon, gallium arsenide, cadmium telluride and others. Herein the term "semiconductor" denotes materials which can conduct electricity when charge carriers are induced by thermal or electromagnetic excitation. The term "photoconductive" generally relates to the process in which electromagnetic radiant energy is absorbed and thereby converted to excitation energy of electric charge carriers so that the carriers can conduct, i.e., transport, electric charge in a material. The terms "photoconductor" and "photoconductive material" are used herein to refer to semiconductor materials which are chosen for their property of absorbing electromagnetic radiation to generate electric charge carriers.

PV devices may be characterized by the efficiency with which they can convert incident solar power to useful electric power. Devices utilizing crystalline or amorphous silicon dominate commercial applications, and some have achieved efficiencies of 23% or greater. However, efficient crystalline-based devices, especially of large surface area, are difficult and expensive to produce due to the problems inherent in producing large crystals without significant efficiency-degrading defects. On the other hand, high efficiency amorphous silicon devices still suffer from problems with stability. Present commercially available amorphous silicon cells have stabilized efficiencies between 4 and 8%.

PV devices may be optimized for maximum electrical power generation under standard illumination conditions (i.e., Standard Test Conditions which are 1000 W/m2, AM1.5 spectral illumination), for the maximum product of photocurrent times photovoltage. The power conversion efficiency of such a cell under standard illumination conditions depends on the following three parameters: (1) the current under zero bias, i.e., the short-circuit current $I_{SC}$, in Amperes (2) the photovoltage under open circuit conditions, i.e., the open circuit voltage $V_{OC}$, in Volts and (3) the fill factor, ff.

PV devices produce a photo-generated current when they are connected across a load and are irradiated by light. When irradiated under infinite load, a PV device generates its maximum possible voltage, V open-circuit, or $V_{OC}$. When irradiated with its electrical contacts shorted, a PV device generates its maximum possible current, I short-circuit, or $I_{SC}$. When actually used to generate power, a PV device is connected to a finite resistive load and the power output is given by the product of the current and voltage, I×V. The maximum total power generated by a PV device is inherently incapable of exceeding the product, $I_{SC} \times V_{OC}$. When the load value is optimized for maximum power extraction, the current and voltage have the values, $I_{max}$ and $V_{max}$, respectively.

A figure of merit for PV devices is the fill factor, ff, defined as:

$$ff = \{I_{max}V^a_m{}_x\}/\{I_{SC}V_{OC}\} \quad (1)$$

where ff is always less than 1, as $I_{SC}$ and $V_{OC}$ are never obtained simultaneously in actual use. Nonetheless, as ff approaches 1, the device has less series or internal resistance and thus delivers a greater percentage of the product of $I_{SC}$ and $V_{OC}$ to the load under optimal conditions. Where $P_{inc}$ is the power incident on a device, the power efficiency of the device, $\eta_P$, may be calculated by:

$$\eta_P = ff^*(I_{SC}*V_{OC})/P_{inc}$$

To produce internally generated electric fields that occupy a substantial volume of the semiconductor, the usual method is to juxtapose two layers of material with appropriately selected conductive properties, especially with respect to their distribution of molecular quantum energy states. The interface of these two materials is called a photovoltaic junction. In traditional semiconductor theory, materials for forming PV junctions have been denoted as generally being of either n or p type. Here n-type denotes that the majority carrier type is the electron. This could be viewed as the material having many electrons in relatively free energy states. The p-type denotes that the majority carrier type is the hole. Such material has many holes in relatively free energy states. The type of the background, i.e., not photo-generated, majority carrier concentration depends primarily on unintentional doping by defects or impurities. The type and concentration of impurities determine the value of the Fermi energy, or level, within the gap between the conduction band minimum and valance band maximum energies. The Fermi energy characterizes the statistical occupation of molecular quantum energy states denoted by the value of energy for which the probability of occupation is equal to ½. A Fermi energy near the conduction band minimum energy indicates that electrons are the predominant carrier. A Fermi energy near the valence band maximum energy indicates that holes are the predominant carrier. Accordingly, the Fermi energy is a primary characterizing property of traditional semiconductors and the prototypical PV junction has traditionally been the p-n interface.

The term "rectifying" denotes, inter alia, that an interface has an asymmetric conduction characteristic, i.e., the interface supports electronic charge transport preferably in one direction. Rectification is associated normally with a built-in electric field which occurs at the junction between appropriately selected materials.

Conventional inorganic semiconductor PV cells employ a p-n junction to establish an internal field. Early organic thin film cell, such as reported by Tang, Appl. Phys Lett. 48, 183 (1986), contain a heterojunction analogous to that employed in a conventional inorganic PV cell. However, it is now recognized that in addition to the establishment of a p-n type junction, the energy level offset of the heterojunction also plays an important role.

The energy level offset at the organic D-A heterojunction is believed to be important to the operation of organic PV devices due to the fundamental nature of the photo-generation process in organic materials. Upon optical excitation of an organic material, localized Frenkel or charge-transfer excitons are generated. For electrical detection or current generation to occur, the bound excitons must be dissociated into their constituent electrons and holes. Such a process can be induced by the built-in electric field, but the efficiency at the electric fields typically found in organic devices (F~$10^6$ V/cm) is low. The most efficient exciton dissociation in organic materials occurs at a donor-acceptor (D-A) interface. At such an interface, the donor material with a low ionization potential forms a heterojunction with an acceptor material with a high electron affinity. Depending on the alignment of the energy levels of the donor and acceptor materials, the dissociation of the exciton can become energetically favorable at such an interface, leading to a free electron polaron in the acceptor material and a free hole polaron in the donor material.

Organic PV cells have many potential advantages when compared to traditional silicon-based devices. Organic PV cells are light weight, economical in materials use, and can be deposited on low cost substrates, such as flexible plastic foils. However, organic PV devices typically have relatively low external quantum efficiency (electromagnetic radiation to electricity conversion efficiency), being on the order of 1% or less. This is, in part, thought to be due to the second order nature of the intrinsic photoconductive process. That is, carrier generation requires exciton generation, diffusion and ionization or collection. There is an efficiency η associated with each of these processes. Subscripts may be used as follows: P for power efficiency, EXT for external quantum efficiency, A for photon absorption, ED for diffusion, CC for collection, and INT for internal quantum efficiency. Using this notation:

$$\eta_P \sim \eta_{EXT} = \eta_A * \eta_{ED} * \eta_{CC}$$

$$\eta_{EXT} = \eta_A * \eta_{INT}$$

The diffusion length ($L_D$) of an exciton is typically much less ($L_D$~50Å) than the optical absorption length (~500Å), requiring a trade-off between using a thick, and therefore resistive, cell with multiple or highly folded interfaces, or a thin cell with a low optical absorption efficiency.

The continued improvement of organic photovoltaic devices (OPVs), including organic photodetectors, and dye-sensitized solar cells (DSSCs) relies on the development of more strongly and broadly absorbing organic chromophores capable of funneling energy to a single excited state to undergo charge separation at a donor/acceptor (D/A) interface as well as managing conduction of carriers generated by the charge separation process. Porphyrins and metalloporphyrins are promising chromophores for these applications due to their high extinction coefficients and reversible electrochemistry. Additionally, metalloporphyrins can be efficient luminophores, allowing them to find applications in organic light-emitting devices (OLEDs). However, these materials are not generally good absorbers across the visible spectrum since (i) the so-called Q transitions are typically much weaker than the highly allowed Soret (or B) transitions and (ii) there is usually a deep absorption minimum in the most intense part of the visible spectrum between the Soret and Q bands.

This lack of broad absorption can be a disadvantage in solar cell applications, where absorption across all wavelengths is desirable in order to maximize external quantum efficiency (EQE), and it can also prove disadvantageous for imaging applications where irradiation at a specific wavelength where porphyrin absorption is weak is desired.

The design of metalloporphyrin scaffolds where 4 appended fluorophores are attached via meso positions in order to fill specific gaps in the porphyrin absorption spectrum, allowing a broadened yet intense absorbance that efficiently generates a metalloporphyrin-based triplet state to be used in, e.g., solar cell and imaging applications. Although the use of antenna chromophores with porphyrins has been reported to lead to spectral broadening and efficient chromophore→porphyrin energy transfer, this strategy typically does not lead to greatly broadened absorbance and has not been utilized for triplet harvesting since the reported examples do not utilize heavy metals that facilitate the intersystem crossing process. Additionally, in the one example where such a complex is used in a solar cell, only modest improvements in absorption and device performance were observed since only one fluorophore antenna was incorporated, leading to only a modest increase in overall absorption. The strategy presented herein has several distinct advantages due to the long lifetimes and large Stokes shifts associated with triplet excited states.

SUMMARY OF THE INVENTION

The present disclosure relates to multichromophoric assemblies comprising metalloporphyrin scaffolds. The present disclosure also relates, in part, to methods for generating electric-field-stabilized geminate polaron pairs comprising applying electric fields to the multichromophoric assemblies described herein, or alternatively, directly to the metalloporphyrins provided by the present disclosure. The present disclosure further relates, in part, to multichromophoric assemblies comprising metalloporphyrin scaffolds, which exhibit enhanced energy transfer properties. Methods of making the metalloporprypherin scaffolds are also contemplated.

In one embodiment, there is disclosed a multichromophoric assembly comprising a metalloporphyrin of Formula I

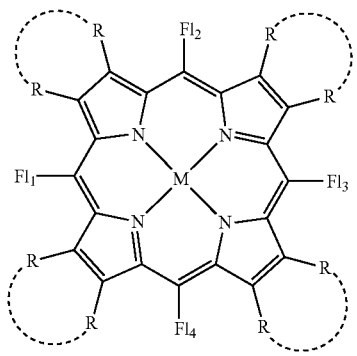

Formula I or salts or tautomers thereof, wherein:
$Fl_1$, $Fl_2$, $Fl_3$ and $Fl_4$ are each independently selected from fluorophores;
IR is selected from H, optionally substituted alkyl, optionally substituted aryl, optionally substituted heteroalkyl, and optionally substituted heteroaryl; or
one or more R groups may be connected to form a cycloalkyl or benzannulated ring system; and
M is a metal optionally bound to one or more additional neutral or anionic ligands.

The foregoing and other features of the present disclosure will be more readily apparent from the following detailed description of exemplary embodiments, taken in conjunction with the attached drawings. It will be noted that for convenience all illustrations of devices show the height dimension exaggerated in relation to the width.

DETAILED DESCRIPTION OF THE INVENTION

A. Multichromophoric Arrays for Photovoltaics

Figure 1:
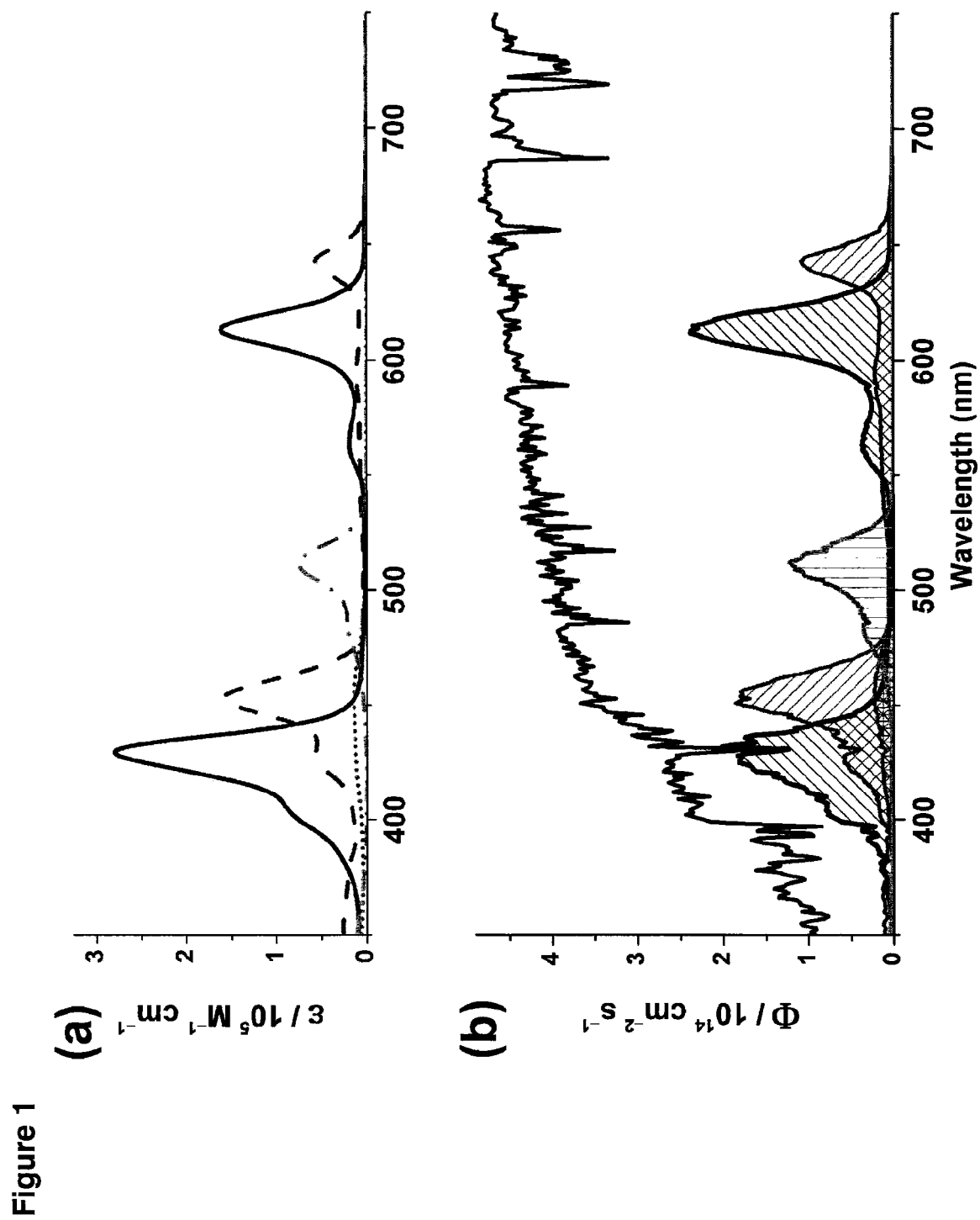
FIG. 1. is a diagram showing (a) UV/Vis spectra of Pt(TPBP) (blue solid), chlorophyll B (red dash), Ru(bpy)$_3^{2+}$ (green dot), and Me$_2$BODIPY (gray dot-dash); (b) Photon flux for AM1.5G (black) plotted with rate of photon absorption for 2 μM solutions of Pt(TPBP) (blue), chlorophyll B (red), Ru(bpy)$_3^{2+}$ (green), and Me$_2$BODIPY (gray dot-dash) in a 1 cm path-length cell.

In one embodiment, the compounds described herein are constructed of multichromophoric arrays where four antennae are appended to a metalloporphyrin scaffold such that (a) four fluorophore antennae are symmetrically disposed about the porphyrin core, (b) there is efficient energy transfer between the constituents, and (c) the metalloporphyrin facilitates intersystem crossing such that photons absorbed by the fluorescent antennae are efficiently funneled to a porphryin-based triplet state that may be utilized in solar cell and imaging applications. This triplet state confers several advantages, e.g., (a) a large Stokes shift that may be utilized to red-shift the emission for imaging purposes and (b) a long excited-state lifetime that may be utilized to improve performance of OPVs. Importantly, the fluorescent antennae attached to the metalloporphyrin core cannot efficiently access such a triplet state and, when they do undergo intersystem crossing, it generally leads to facile deactivation rather than phosphorescence.

Aside from meeting a variety of materials criteria, promising candidates usually exhibit high absorptivities over a range of wavelengths to harvest the greatest possible fraction of available light. This criterion is important for devices employing organic thin films, for which exciton diffusion and carrier conduction can impose strict limits on the ideal thickness of active layers. One promising strategy is described herein, that is, the construction of multichromophoric arrays capable of efficient intramolecular energy transfer between two or more highly absorbing components. This approach has been used in a range of systems, in which "antenna" chromophores transfer energy to a central chromophore, reminiscent of the energy transfer relays in photosynthetic organisms such as purple bacteria.

Researchers have used dendrimers as synthetic mimics of these assemblies, with antennae arranged around central chromophores to optimize the energy transfer process, generating so-called core-shell systems with a "shell" of antenna chromophores surrounding a lower energy core. While the core-shell approach can give good spectral coverage since both the core and shell absorbance can be used to excite the central chromophore, it often leads to isolation of the core chromophore, preventing effective energy-harvesting from the core-shell system. Thus, while Förster energy transfer can efficiently transfer energy into the core, extraction of charge from the excited core, an important step in OPVs, is hindered by the resistance of the shell materials to transport charge into or out of the core. In one embodiment a core-shell system that efficiently captures a broad spectrum is described herein, using both antennae and core chromophores, and shows quantitative energy transfer from the antennae to core, but at the same time delocalizes the excited state energy over both the core and shell chromophores. In one embodiment, this has been achieved by adjusting the singlet and triplet energies of the core and shell materials to achieve efficient singlet energy transfer from shell to core while maintaining closely matched triplet energies to achieve a balanced distribution of triplet energy between the core and shell.

In addition to designing core and shell chromophores that achieve efficient singlet energy transfer and triplet equilibrium between core and shell, materials that result in a net absorbance showing broad coverage of the solar spectrum are described herein. One advantage of using complexes with panchromatic transitions may be easily demonstrated by comparison of solar dyes in the context of solar radiation.

In FIG. 1a, UV/Vis extinction spectra are presented for two common chromophores, tris(bipyridyl)ruthenium(II) and chlorophyll B, along with platinum tetraphenyltetrabenzoporphyrin (Pt(TPBP), Chart 1), a triplet material recently shown in lamellar OPVs, and Me$_2$BODIPY (Chart 1), a dye with absorbing properties complementary to those of Pt(TPBP). Compounds described herein, such as, for example, Pt(TPBP) and Me$_2$BODIPY may be used as the core and shell, respectively, in the light-harvesting system described herein. In FIG. 1b, the extinction spectra are translated into a rate of photon absorption under AM1.5G sunlight for a 2 µM solution of each molecule. The percentage of photons absorbed can be calculated by a ratio of the integrated area under each curve to the integrated AM1.5G flux (black trace), automatically correcting for the fact that photon flux varies with wavelength.

Chart 1. Representative model complexes described herein.

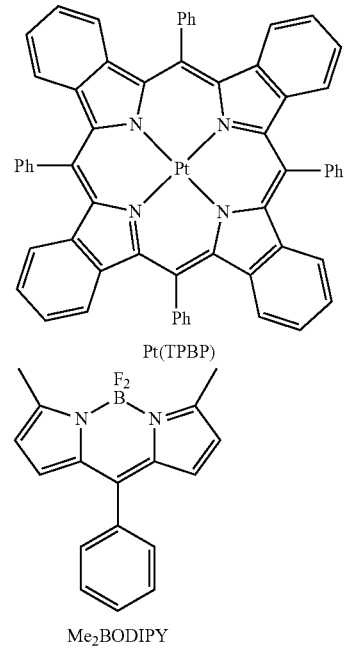

Pt(TPBP)

Me$_2$BODIPY

In one embodiment, the compounds herein exhibit high absorptivities over a range of wavelengths to harvest the greatest possible fraction of available light.

In another embodiment, the compounds herein efficiently capture a broad spectral coverage, using both antennae and core chromophores, and show quantitative energy transfer from the antennae to core. In another embodiment, the compounds described herein further delocalize the excited state energy over both the core and shell chromophores.

In one embodiment, at low concentration, the percentage of photons absorbed roughly follows the integrated absorption coefficient (Table 1), and by this measure Pt(TPBP) appears to perform better than Ru(bpy)$_3^{2+}$ and chlorophyll B. However, a more illuminating comparison is given by the 50% photon capture threshold (PCT[50]), the concentration of a molecule required to absorb 50% of incident solar photons between 350 and 750 nm. With its narrow transitions spanning a comparatively small portion of the visible spectrum, Pt(TPBP) exhibits a higher PCT[50] than chlorophyll B because the sharp transitions of Pt(TPBP) quickly become saturated and little absorption is achieved from 450 to 550 nm.

TABLE 1

Visible-light[a] absorption properties of representative chromophores referenced to AM1.5G photon flux

| Complex | Integrated Absorption Coefficient (M$^{-1}$) | AM1.5G Photon Capture (1 µM, 10 µM)[a,b] | 50% Photon Capture Threshold[a,c] |
|---|---|---|---|
| Ru(bpy)$_3^{2+}$ | 0.70 × 10$^8$ | 0.6%, 5.1% | ~1000 µM |
| Chlorophyll B | 3.8 × 10$^8$ | 3.8%, 24% | 43 µM |

TABLE 1-continued

Visible-light[a] absorption properties of representative chromophores referenced to AM1.5G photon flux

| Complex | Integrated Absorption Coefficient (M$^{-1}$) | AM1.5G Photon Capture (1 µM, 10 µM)[a,b] | 50% Photon Capture Threshold[a,c] |
|---|---|---|---|
| Pt(TPBP) | 6.2 × 10$^8$ | 5.5%, 26% | 55 µM |
| Me$_2$BODIPY | 1.1 × 10$^8$ | 1.4%, 9.7% | ~2000 µM |
| Pt(TPBP) + 4 Me$_2$BODIPY | 11 × 10$^8$ | 10%, 43% | 15 µM |

[a]350-750 nm.
[b]Percentage of incident solar photons absorbed for a solution of a given concentration (1 cm path length).
[c]Concentration required to absorb 50% of the incident solar photons (1 cm path length).

Boron dipyrrin (BODIPY) dyes such as Me$_2$BODIPY have been widely studied for imaging applications and exhibit high molar absorptivities in the 450-550 nm range, precisely where absorption by Pt(TPBP) is weakest. In addition, since these molecules are intensely fluorescent between 500 and 600 nm, it is expected that Förster resonant energy transfer (FRET) from BODIPY to Pt(TPBP) would be fast and efficient, consistent with previous results showing that BODIPY chromophores can serve as effective antennae for porphyrins.

As seen from Table 1, the Me$_2$BODIPY complex exhibits lackluster absorption properties by itself due to its single sharp visible transition. However, if four Me$_2$BODIPY molecules were coupled to Pt(TPBP), the absorptions of the two species would be both balanced and complementary (Table 1), leading to dramatically improved properties relative to Pt(TPBP) alone. Therefore, the combination of Pt(TPBP) and Me$_2$BODIPY chromophores into a single complex would lead to a multichromophoric complex with attractive visible-light absorption properties rivaling or exceeding the best chromophores for solar energy harvesting (e.g., chlorophyll B).

Compounds described herein, such as a complex consisting of one Pt(TPBP) and four M$_2$BODIPY moieties in a core-shell arrangement, which efficiently covers the visible spectrum, as illustrated in FIG. 1 and Table 1, and at the same time gives the desirable energy transfer properties for core-shell materials described above, namely singlet funneling to the core followed by triplet redistribution between the core and shell.

Figure 2:
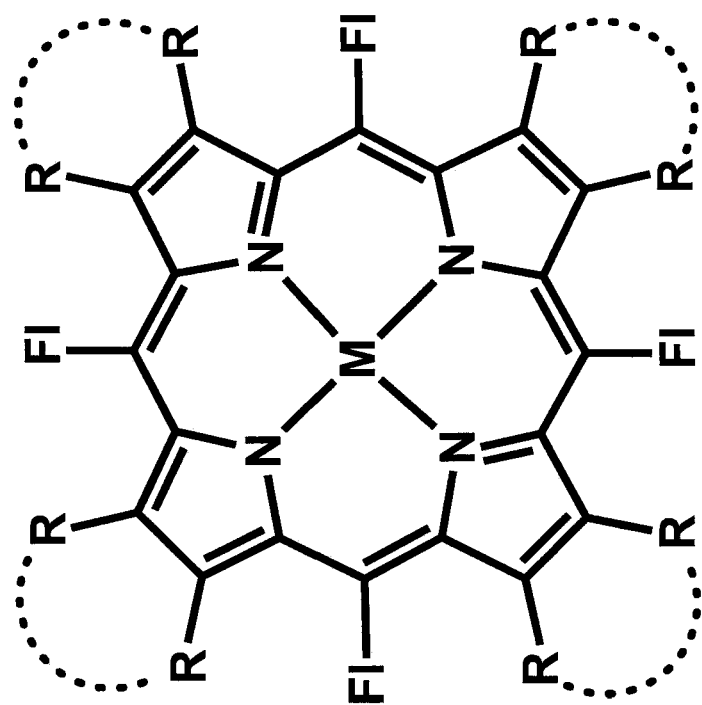
FIG. 2. is a schematic showing prototypical metalloporphyrin multichromophoric assembly for triplet harvesting.

In one embodiment, the compounds described herein comprise a metalloporphyrin core with fluorophores attached as antennae to each meso position, as shown in FIG. 2. The central metal is a heavy atom that facilitates intersystem crossing from the singlet to the triplet excited state to facilitate full conversion of absorbed photon to triplet excitons. "M" may also designate such a metal with other bound ligands, and the overall complex may be neutral or positively charged with compensating counter-anions. Possible metal centers include Y, La, Zr, Hf, Nb, Ta, Mo, W, Tc, Re, Ru, Os, Rh, Ir, Pd, Pt, Ag, Au, Cd, and Hg; the heavy main group metalloids Ga, Ge, In, Sn, Sb, Tl, Pb, and Bi; lanthanides and actinides. In any of these cases, one or more additional neutral or anionic ligands may be bound to the metal center, especially heterocycles such as pyridine, imidazole, pyrazine, furan, and thiophene, as well as halides (F, Cl, Br, I) and pseudo-halides such as sulfonates (e.g., trifluoromethanesulfonate) and carboxylates (e.g., acetate).

The porphyrin core may be unsubstituted at the β positions (R=H). Additionally, the core may be substituted with R=alkyl, aryl, heteroalkyl, or heteroaryl. The dashed lines in FIG. 1 indicate that R groups may be connected to form cycloalkyl or benzannulated substituents, such as the cyclohexenoporphryin described as compound 2 in the example below or the benzoporphyrin presented as compound 3 (Pt($^{BDP}$TPBP)) in the example below. Due to their strong Q bands that help to broaden overall absorption from the complex, benzoporphyrins, naphthoporphyrins, and anthracenoporphyrins are especially important members of the class of porphyrins described here.

The fluorophore antennae (designated "Fl" in FIG. 2 and hereafter) may be any molecules that meet the following requirements: (1) strong absorption either at higher energy than the porphyrin Soret or at intermediate energy between the porphyrin Soret and Q band(s); (2) efficiently transfers energy from the photoexcited state to the metalloporphyrin core (e.g., by Förster resonant energy transfer (FRET)). Possible fluorophore antennae include boron dipyrrin (BODIPY, see Example compounds 2 and 3), pyrene, fluorescein, and merocyanine-based dyes. These dyes may be directed attached to the meso position or may be attached via a linker, such as an alkyl or phenylene, in order to make energy transfer as efficient as possible while not imposing drastic steric constraints on the molecule that prevent assembly or have a deleterious effect on the photophysics of the porphyrin core.

In one embodiment, the present disclosure relates to a multichromophoric assembly comprising a metalloporphyrin of Formula I

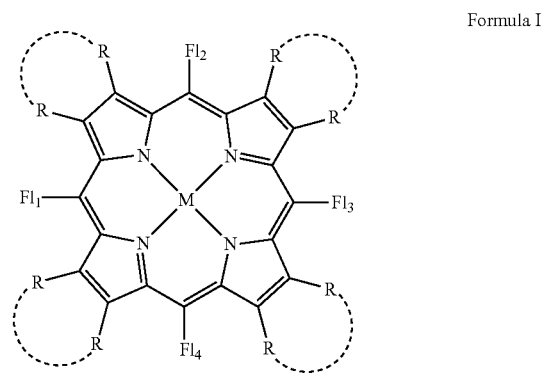

Formula I or salts or tautomers thereof, wherein:
Fl$_1$, Fl$_2$, Fl$_3$ and Fl$_4$ are each independently selected from fluorophores;
R is selected from H, optionally substituted alkyl, optionally substituted aryl, optionally substituted heteroalkyl, and optionally substituted heteroaryl; or
one or more R groups may be connected to form a cycloalkyl or benzannulated ring system; and
M is a metal optionally bound to one or more additional neutral or anionic ligands.

In another embodiment of metalloporphyrins of Formula I, M is selected from Y, La, Zr, Hf, Nb, Ta, Mo, W, Tc, Re, Ru, Os, Rh, Ir, Pd, Pt, Ag, Au, Cd, Hg, Ga, Ge, In, Sn, Sb, Ti, Pb, Bi, lanthanides, and actinides. In another embodiment, M is selected from Ga, Ge, In, Sn, Sb, Ti, Pb, and Bi. In another embodiment, M is Ti. In further embodiments, M is bound to one or more heterocycles, halides, and pseudohalides.

In one embodiment of metalloporphyrins of Formula I, the heterocycles are selected from pyridine, imidazole, pyrazine, furan and thiophene.

In one embodiment of metalloporphyrins of Formula I, the pseudo-halides are selected from sulfonates and carboxylates.

In one embodiment of metalloporphyrins of Formula I, the sulfonates are trifluoromethanesulfonate groups and at the carboxylates are acetate groups.

In one embodiment of metalloporphyrins of Formula I, $Fl_1$, $Fl_2$, $Fl_3$ and $Fl_4$ are each independently selected from boron dipyrrin, pyrene, fluorescein, and merocyanine-based dyes. In another embodiment of metalloporphyrins of Formula I, $Fl_1$, $Fl_2$, $Fl_3$ and $Fl_o$ are each 4,4-difluoro-4-bora-3a,4a-diaza-s-indacene.

In one embodiment of metalloporphyrins of Formula I, said dyes are directly attached to the metalloporphyrin scaffold or are attached via a linker.

In one embodiment of metalloporphyrins of Formula I, said linker comprises an alkyl or phenylene.

In one embodiment of metalloporphyrins of Formula I, adjacent R groups are connected to form a cyclohexene ring, benzene ring, or combination thereof.

In one embodiment of metalloporphyrins of Formula I, the cycloalkyl or benzannulated ring system comprise porphyrins.

In one embodiment of metalloporphyrins of Formula I, wherein the porphyrins comprise benzoporphyrins, naphthoporphyrins, and anthracenoporphyrins.

In one embodiment, the metalloporphyrin of Formula I is

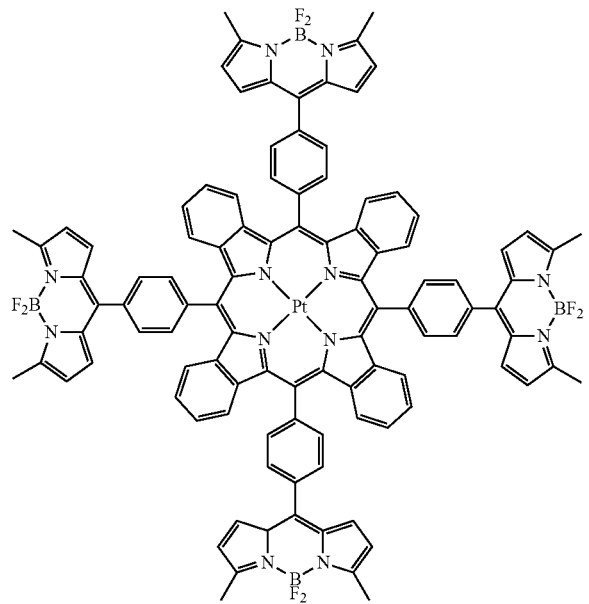

or salts or tautomers thereof.

In one embodiment the metalloporphyrins of Formula I further comprising at least one triplet forming dopant material.

In one embodiment of metalloporphyrins of Formula I, the fluorophores exhibit a) strong absorption either at higher energy than the porphyrin Soret or at intermediate energy between the porphyrin Soret and Q band(s); or b) efficient transfer of energy from the photoexcited state to the metalloporphyrin core.

B. Electric-Field-Stabilized Polar Pair Materials

In another embodiment, there is disclosed the tetrasubstituted porphyrin compounds comprising their use as chromophores for the generation of electric-field-stabilized geminate polaron pairs. These polaron pairs collapse in the absence of an electric field, generating a high concentration of excitons and may be useful for the construction of organic lasers. In this process a large electric field is applied to drive the charge separation of excitons formed on light absorption and stabilize the geminate polaron pairs toward recombination. This has been accomplished with a lightly doped matrix, where the dopant absorbs light and acts as one of the polarons (cation or anion), with the other polaron on the matrix material. The porphyrins being described here have donor and acceptor present in the same molecule (porphyrin forms one polaron and the meso substituent forms the other), such that charge separation to form the geminate pairs can be efficiently achieved within the chromophore itself. This allows the chromophore to be doped into nonconductive host materials, preventing carrier leakage.

Figure 3:
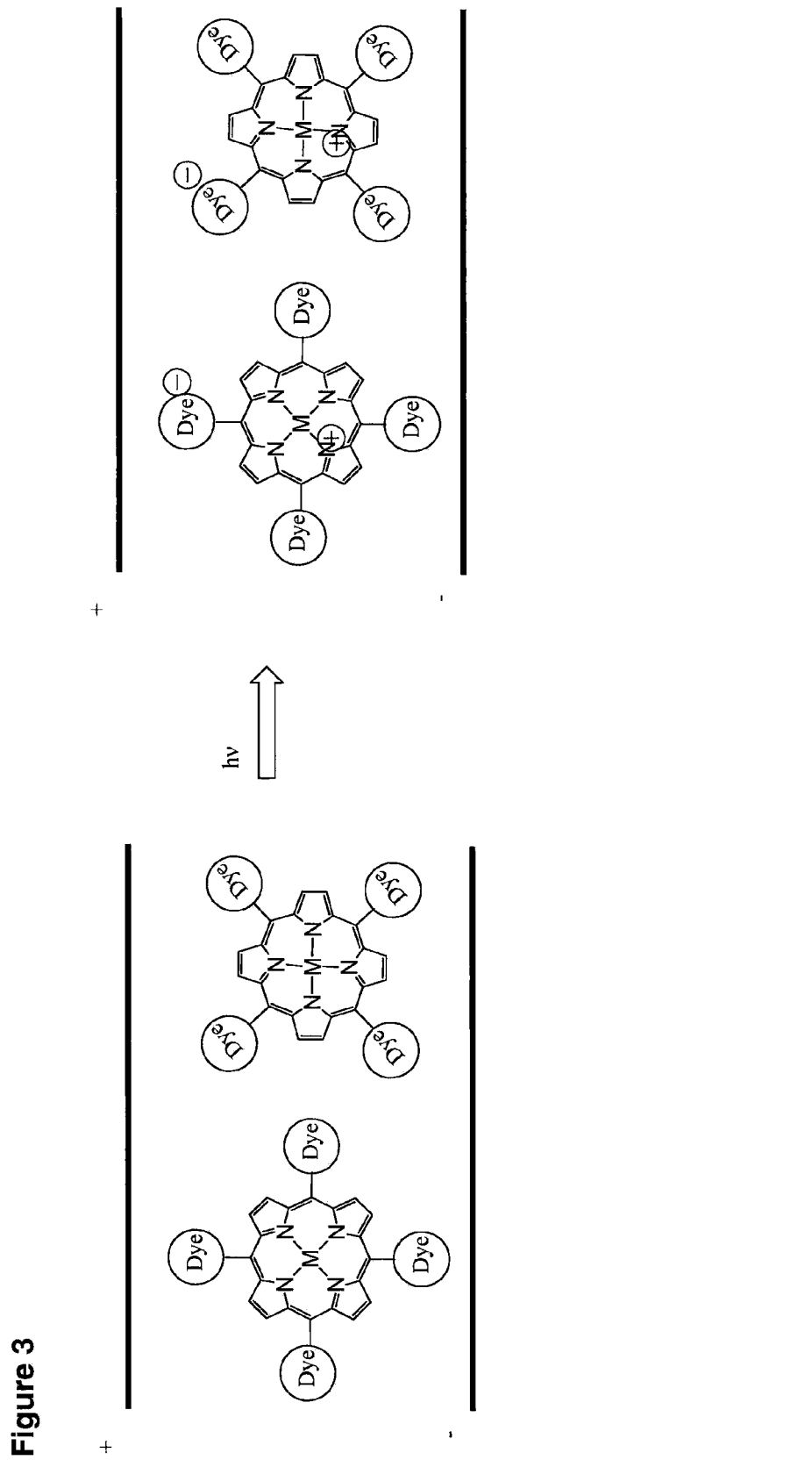
FIG. 3. is a schematic showing charge separation in porphyrin(dye)$_4$ complexes.

The inherent $C_4$ symmetry of the substituted porphryins will ensure that every molecule is present in an orientation that will promote charge separation (see FIG. 3). The only orientation that cannot be efficiently coupled with the electric field is one in which the plane of the porphryin in perpendicular the other applied electric field. Fortunately, a randomly doped film will have a low percentage of the dopant present in this nonproductive orientation.

C. Experimental

The desired porphyrin-based multichromophoric arrays may be assembled under standard Lindsey conditions (Scheme 1a), or may be constructed by cross-coupling reactions from meso-halogenated (or meso-pseudohalogenated) porphyrin precursors (Scheme 1b). Both methods are well precedented, and importantly they allow integration of the desired fluorophore into the porphyrin framework either during or after porphyrin assembly. After synthesis of the porphyrin-fluorophore array, numerous modifications may be made such as oxidation or substitution of R and R' (see example) as well as substitution of M with another metal (in Scheme 1, M may indicate any transition metal or main group metalloid as well as the free base porphyrin). However, it is desired that the metal finally used in the complex be one that facilitates efficient intersystem crossing to the metalloporphyrin triplet state.

Synthesis and Characterization of Pt($^{BDP}$TPBP)

As mentioned above, platinum tetraphenyltetrabenzoporphyrin (Pt(TPBP)) has been identified as a promising material for lamellar organic photovoltaics (OPVs), affording devices with power conversion efficiencies approaching 2%. However, since Pt(TPBP) has weak absorptivity in the middle of the visible spectrum (450-550 nm), where solar radiation is quite intense, the inventors investigated integrating the complex into a multichromophoric array with boron dipyrrin (BODIPY) chromophores since their absorptions would complement those of the benzoporphyrin and the similar triplet energies of the Pt(TPBP) and BODIPY molecules might allow fine tuning of the light-harvesting properties of the resulting array. Employing parameters derived from model $Me_2$BODIPY and Pt(TPBP) complexes and assuming a separation of 10 Å, a high FRET efficiency (>99.9%) and rate ($k_{FRET}$=8.3×10$^{11}$ s$^{-1}$) were predicted using the PhotochemCAD software package.

The BODIPY-benzoporphyrin scaffold was assembled following the strategy of Finikova et al. (Scheme 1). Cyclohexenoporphyrin 2, with four BODIPY units connected to the meso positions by phenylene linkers, was accessed in 35% yield via an acid-catalyzed macrocyclization of 4,5,6,7-tetrahydroisoindole and BODIPY derivative 1 with a para aldehyde functionality. Platination and oxidation of 2 were performed as previously described for the related Pt(TPBP)

complex, ultimately affording 4 in pure form as a dark green-black solid in 10% yield over two steps, as described herein.

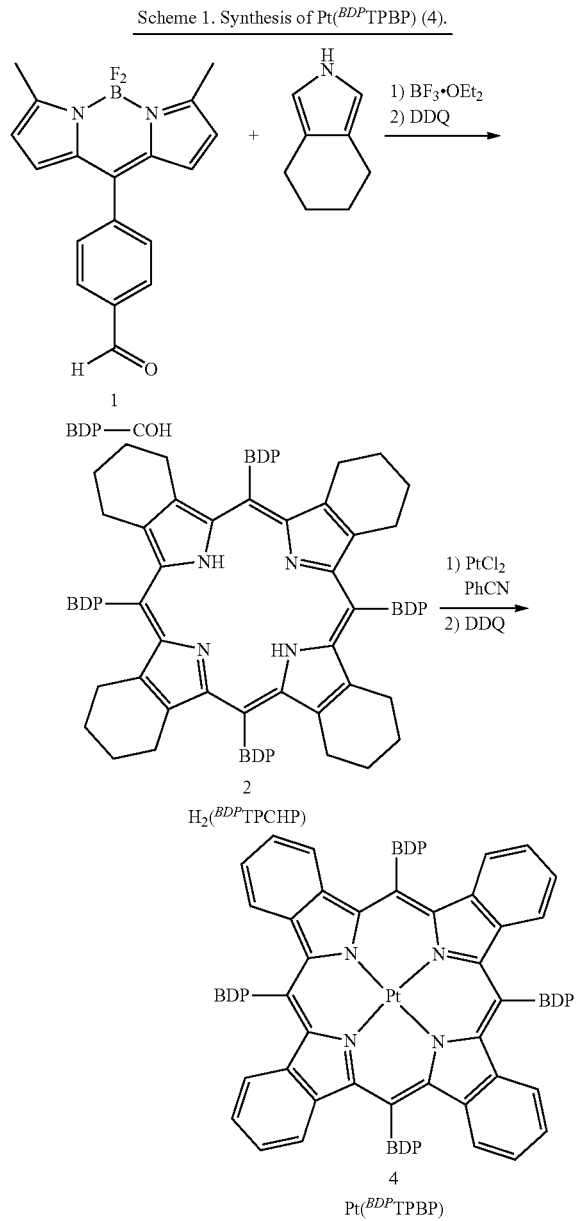

Scheme 1. Synthesis of Pt($^{BDP}$TPBP) (4).

Figure 4:
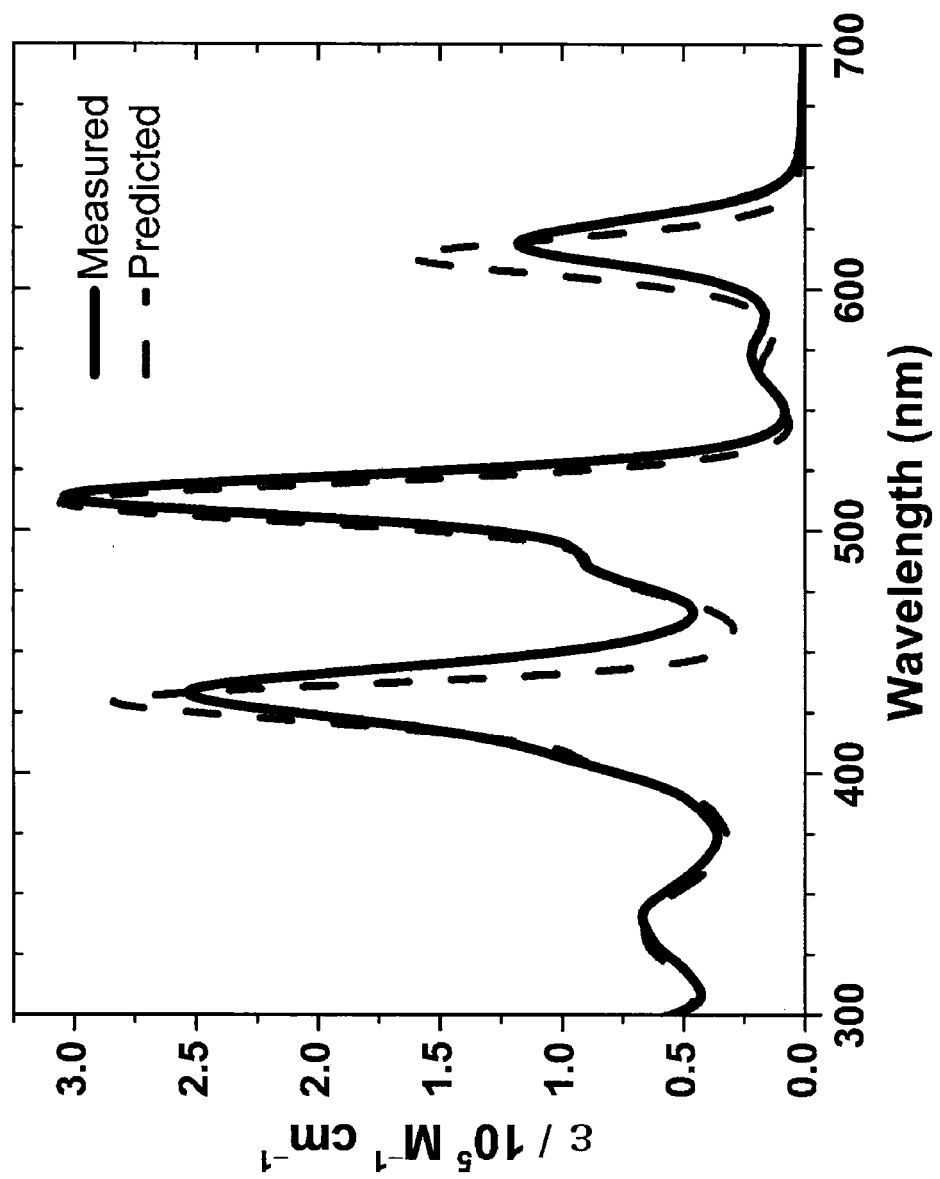
FIG. 4. is a diagram showing predicted (dashed) and measured (solid) UV/Vis spectra for 4 in CH$_2$Cl$_2$.

The UV/Vis spectrum of 4 is presented in FIG. 4 along with the spectrum predicted from Pt(TPBP) and four Me$_2$BODIPY model complexes. As expected, the absorption profile of 4 is a composite of those for the model complexes, with exceptionally intense transitions across the visible spectrum. Although the peak at 514 nm ascribed to the BODIPY units is quite similar to that of Me$_2$BODIPY, the Soret and Q peaks characteristic of the benzoporphyrin are broadened relative to Pt(TPBP). For instance, the Soret band at 433 nm exhibits a full width at half maximum (FWHM) of 35 nm, compared with 22 nm for Pt(TPBP), and the FWHM for the Q band at 619 nm has increased from 19 nm for Pt(TPBP) to 24 nm for 4. The porphyrin peak broadening may be due to conformational disorder and the accompany-ing molecular distortion of the BODIPY units. This broadening leads to a small improvement in photon capture properties relative to those predicted for 4 (AM1.5G Photon Capture (1 μM)=11% (measured), 10% (predicted); PCT$^{50}$=12 μM (measured), 15 μM (predicted)), though the integrated absorption coefficient is unchanged.

Figure 5:
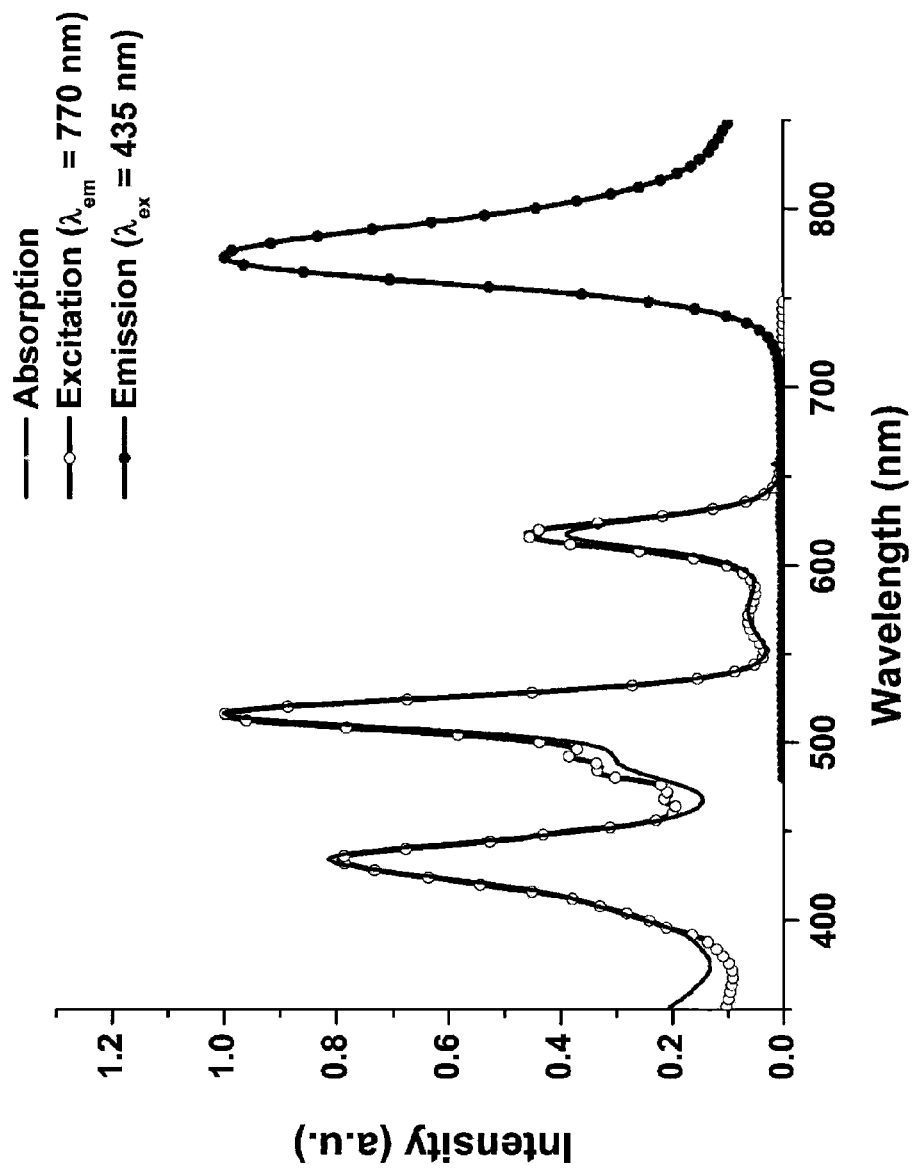
FIG. 5. is a diagram showing normalized absorption, excitation ($\lambda_{em}$=770 nm), and emission ($\lambda_{ex}$=435 nm) spectra of 4 in toluene.

Panchromatic absorption in a multichromophoric array is only useful if efficient energy transfer between the components can be realized, so we turned to photoluminescence (PL) measurements to examine the fate of absorbed photons. At room temperature in toluene, irradiation of the porphyrin at 435 nm leads to near-infrared (NM) phosphorescence ($\lambda_{em}$=772, FIG. 5) along with extremely weak porphyrin fluorescence ($\lambda_{em}$=628 nm, $\phi_{fl}$<0.001), similar to what has previously been reported for metal-benzoporphyrin complexes. An excitation spectrum for this 772 nm emission closely parallels the absorption spectrum of 4 (FIG. 5), indicating that intramolecular energy transfer is quite efficient, as expected. Thus, direct excitation of the BODIPY subunit at 500 nm results in nearly exclusive (>98%) phosphorescent emission at 772 nm.

Recent studies have indicated that the triplet state of BODIPY may reside close in energy to the observed emission at 772 nm, suggesting that the lowest-lying excited state of BODIPY-benzoporphyrin hybrids may be precisely controlled by independent tuning of the BODIPY and porphyrin subunits. However, the phosphorescence efficiency (26%) and lifetime (τ=67 μs) in toluene are similar to those previously reported for platinum benzoporphyrins, as opposed to much lower efficiencies and millisecond lifetimes reported for sensitized triplet emission from the organic BODIPY fragment. Therefore, emission was assigned to phosphorescence from the platinaporphyrin moiety. Nevertheless, such considerations do not exclude the possible influence of a nonemissive BODIPY triplet on the excited state properties (vide infra).

The behavior of 4 in rigid matrices closely parallels what is observed in solution. At 77K, a single intense NIR phosphorescent emission is observed at 764 nm (τ=92 μs), with quantitative BODIPY→porphyrin energy transfer. The PL behavior of 4 doped (0.5%) into a poly(methyl methacrylate) (PMMA) matrix showed analogous behavior, with efficient energy transfer and long lifetimes (τ=95 μs), though the quantum efficiency ($\phi$=0.17) is slightly lower than in fluid toluene solution, due to a decreased radiative decay rate (kr=3.9×103 s$^{-1}$ in toluene, 1.8×103 s$^{-1}$ in PMMA; knr=1.1×104 s$^{-1}$ in toluene, 8.7×103 in PMMA). Neat films of 4, on the other hand, display only a broad, red-shifted emission (935 nm) at 77 K (Figure S9), indicating competitive deactivation in the neat solid by excimer formation, as previously observed for Pt(TPBP).

Femtosecond Transient Absorption: Observation of Bidirectional Singlet and Triplet Energy Transfer Although steady-state PL measurements suggested that irradiation of 4 led to benzoporphyrin-based phosphorescence, they did not reveal any details of the energy-transfer processes leading to emission. For instance, although irradiation of the BODIPY (BDP) unit leads to porphyrin (Por) phosphorescence, steady-state studies do not discriminate between (a) BDP→Por singlet energy transfer (ST) followed by intersystem crossing (ISC) to give $^3$Por and (b) intersystem crossing at BODIPY followed by BDP→Por triplet energy transfer (TT) to give $^3$Por after excitation of the BODIPY antennae. Previous results have shown that intersystem crossing occurs for platinum benzoporphyrins within several hundred femtoseconds following excitation. On the other hand, time-resolved studies have previously shown that ISC for BODIPY derivatives in the absence of a heavy atom is quite slow (>5 ns). Given the >9 Å separation of the BODIPY and the platinum center (determined by a PM3 minimization), it is most likely that BDP→Por energy transfer precedes ISC, but steady-state measurements cannot rule out the alternative of ISC prior to energy transfer.

Figure 6:
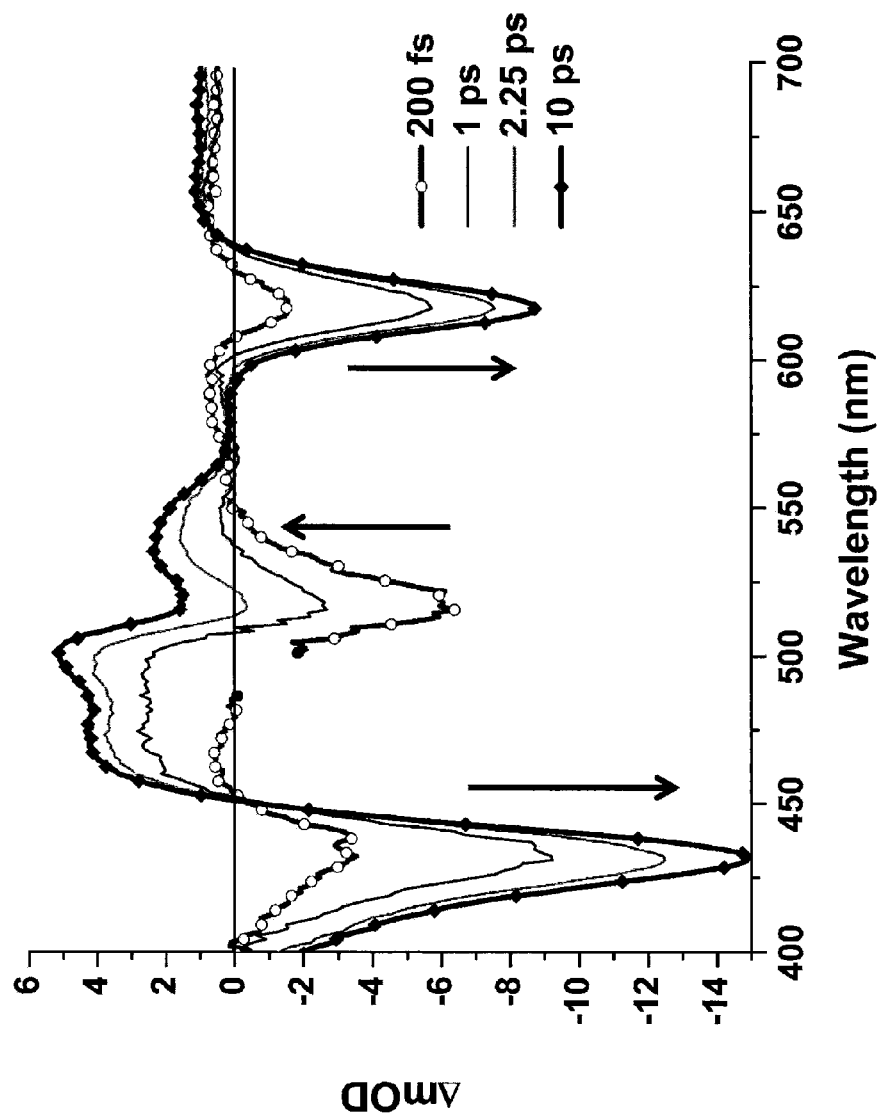
FIG. 6. is a diagram showing ultrafast transient absorption spectra of 4 in toluene after excitation at 508 nm (0.2-10 ps).

Studies to discriminate between these possibilities using ultrafast transient absorption to observe energy transfer and intersystem crossing events occurring within 1 ns of excitation led to the observation of two distinct energy-transfer processes. First, upon selective BODIPY excitation at 508 nm, a bleach of the BODIPY absorption (515 nm) corresponding to immediately appears due to the formation of $^1$BDP*, then recovers over a period of ca. 10 ps with a simultaneous growth of bleaches corresponding to the benzoporphyrin Soret and Q bands (FIG. 6). A global fit to the data yielded a BDP→Por singlet energy transfer rate of $1/k_{ST}$=1.29±0.11 ps (FIG. 7$b$), which is quite similar to the rate predicted for FRET using the model Me$_2$BODIPY and Pt(TPBP) complexes ($1/k_{FRET}$=1.2 ps, vide supra). This observation rules out the possibility of fast intersystem crossing on the BODIPY moieties facilitated by the presence of platinum. The transient spectrum obtained after 10 ps closely resembles those reported for the Pt(TPBP) triplet, consistent with previous measurements revealing a rate of intersystem crossing for Pt(TPBP) of $1/k_{ISC}$=400 fs and indicating that the generation of $^1$Por* by ST from $^1$BDP* is followed by fast and quantitative intersystem crossing to produce $^3$Por.

Figure 7:
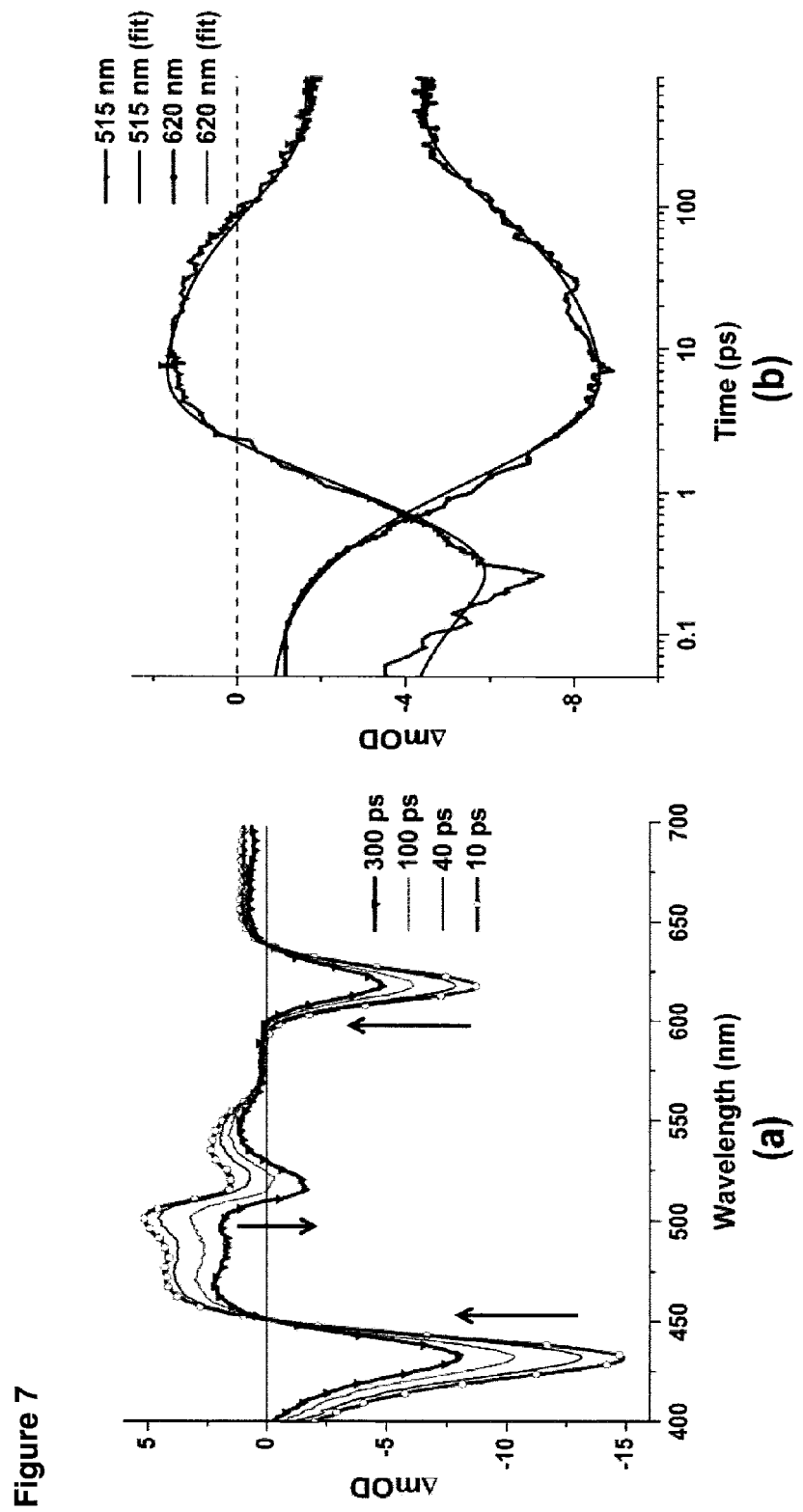
FIG. 7. is a diagram showing (a) Ultrafast transient absorption spectra of 4 after excitation at 508 nm (10-300 ps). (b) Time domain slices of transient absorptions at 515 nm (BODIPY) and 620 nm (porphyrin) with predicted traces based on kinetic parameters for the system.

A longer-time regime, due to Por→BDP triplet energy transfer, was observed from 10-300 ps as the TA bleaches corresponding to the benzoporphyrin partially recovered with the concomitant partial return of the BODIPY bleach at 515 nm (FIG. 7$a$). These spectral changes were modeled to afford an extremely fast rate for Por→BDP triplet energy transfer of $1/k_F$=99.6±7.1 ps. This TT process establishes an equilibrated [$^3$BDP][$^1$Por]-[$^1$BDP][$^3$Por] state in ca. 300 ps, which does not develop further on the time-scale of the experiment. The interplay between BODIPY and porphyrin excited states can be observed in FIG. 7$b$, where the transient absorbances at 515 nm (BODIPY) and 620 nm (porphyrin) are plotted versus time, along with fits associated with the kinetic parameters presented above, following selective BODIPY excitation. The 50% recovery of the Soret and Q bleaches from 10 to 800 ps supports roughly equal populations of the $^3$BDP and $^3$Por states several hundred picoseconds after excitation and indicates a redistribution of energy from the porphyrin core back onto BODIPY antennae in the form of a triplet excited state. This hypothesis is supported by the fact that the transient spectrum in obtained at 300 ps exhibits the combined features of similar spectra reported for BODIPY and platinabenzoporphyrin triplets.

Figure 8:
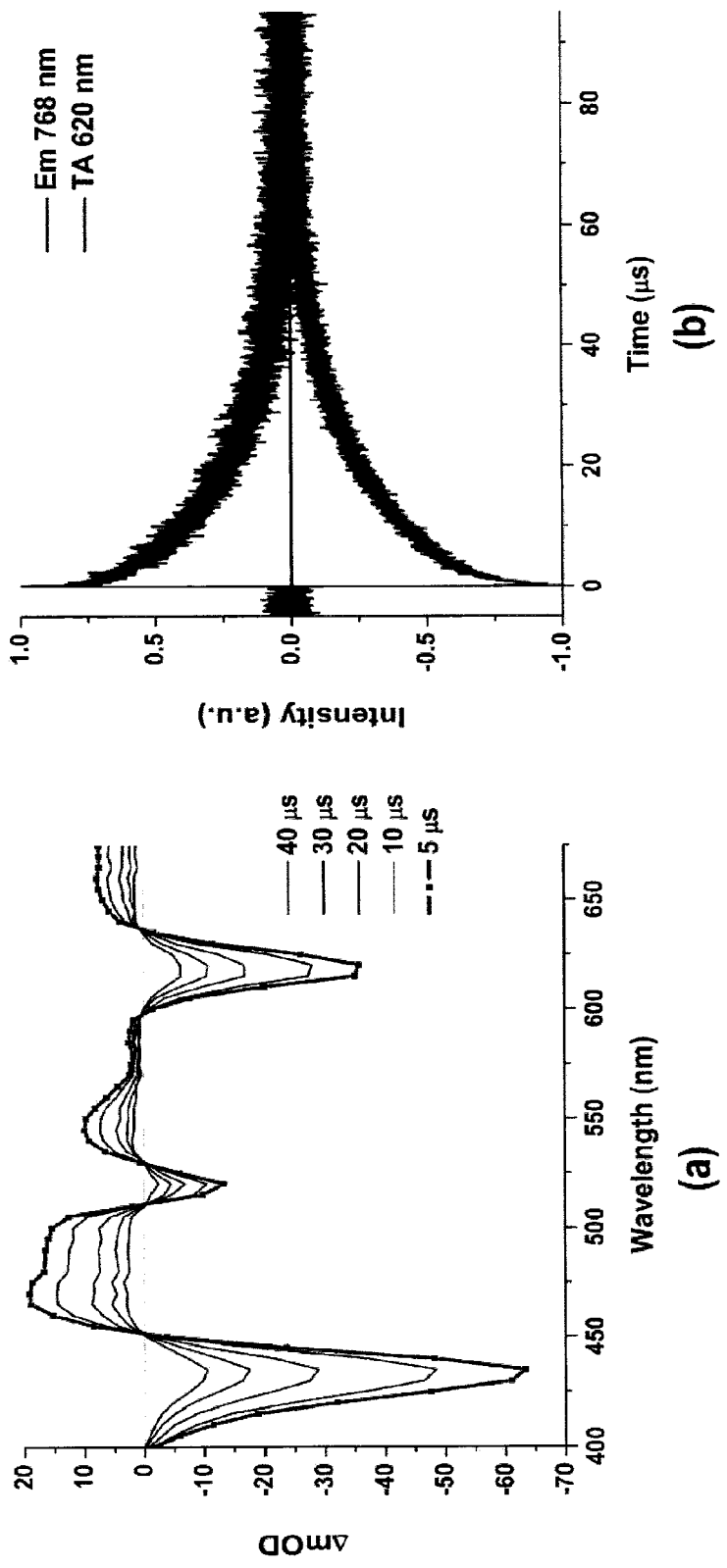
FIG. 8. is a diagram showing (a) Nanosecond transient absorption spectra of 4 following excitation at 487 nm. (b) Normalized phosphorescent decay of 4 and restoration of bleach at 620 nm, monitored by time-resolved transient absorption spectroscopy.

Nanosecond Transient Absorption: Characterization of an Equilibrated Emissive State To further examine the interplay of BODIPY and platinum porphyrin triplet states observed by femtosecond transient absorption, nanosecond-resolved TA measurements was employed to further examine the nature of the long-lived, phosphorescent state of 4. As shown in FIG. 8$a$, excitation of the BODIPY moiety at 487 nm leads to a transient absorption spectrum that is dominated by bleaches corresponding to the benzoporphyrin Soret and Q bands (435 nm and 620 nm, respectively), but also contains a distinct bleach of the BODIPY absorbance (515 nm), and is essentially unchanged from the spectra recorded at 800 ps (vide supra). All features in the transient spectrum decay at the same rate, which matches the rate of phosphorescent decay ($\lambda_{em}$=768 nm) measured for the same solution (FIG. 8$b$). Taken together, these findings show that the long-lived state generated upon excitation of BODIPY consists of BODIPY and benzoporphyrin triplets that reach thermal equilibrium within several hundred picoseconds of excitation. Since the energy transfer leading to equilibration of the triplets ($10^{10}$ s$^{-1}$) is much faster than phosphorescent decay ($10^5$ s$^{-1}$), the ratio of the species remains constant over the phosphorescent lifetime.

The observation of fast thermal equilibration of these two states allows two calculations to be made regarding the dynamics of the molecule. First, the thermal equilibrium between porphyrin triplet ($^3$Por) and BODIPY triplet ($^3$BDP) may be described using a Boltzmann distribution, allowing the energy of $^3$BDP to be estimated if the relative populations of $^3$Por and $^3$BDP are known. The energy difference between two states in thermal equilibrium is given by:

$$\Delta E = E_2 - E_1 = kT \cdot \ln\left(\frac{d_1 P_2}{d_2 P_1}\right) \quad (1)$$

where $d_n$ represents the degeneracy of state n, and $P_n$ represents the population of state n. Since there are four BODIPY antennae surrounding the porphyrin core, the $^3$BDP state is regarded as quadruply degenerated, whereas $^3$Por is doubly degenerated due to its $^3E_u$ state, giving ($d_{BDP}/d_{Por}$)=2. After scaling the observed bleaches by the respective extinction coefficients for the BODIPY and benzoporphyrin portions of complex 4, keeping in mind that the ground-state absorption attributed to BODIPY corresponds to the absorption of four BODIPY units, the relative populations of $^3$Por and $^3$BDP in the equilibrium were estimated to be 0.45 and 0.55, respectively. From these populations, $\Delta E$ was calculated to be 0.5 kT, or 100 cm$^{-1}$ (12 meV) under experimental conditions (T=293 K), allowing the energy of $^3$BDP to be estimated at 766 nm, quite similar to the value reported for phosphorescence from a closely related BODIPY chromophore, and confirming that the two triplets are nearly isoenergetic. These values are also supported by the ca. 50% restoration of the bleaches corresponding to $^3$Por between 10 and 800 ps mentioned above.

Second, the thermal equilibrium between $^3$BDP and $^3$Por excited states leads to an "energy reservoir" effect, similar to that previously described for polycyclic aromatic hydrocarbons (e.g., pyrene, naphthalene) attached to metal complexes. This effect leads to a lengthening of the observed lifetime according to the following equation when the states are in fast equilibrium:

$$\frac{1}{\tau_{obs}} = \frac{P_1}{\tau_1} + \frac{P_2}{\tau_2} \quad (2)$$

where $P_n$ and $\tau_n$ represent, respectively, the relative population and lifetime of state n. Based on the relative populations of $^3$BDP and $^3$Por determined above, and assuming that $\tau_{BDP} \gg \tau_{Por}$, the observed lifetime of 67 µs in dilute toluene represents a 37 µs extension relative to the phosphorescent lifetime expected for the porphyrin in the absence of an energy reservoir (30 µs). This calculated value is quite close to known related complexes adding credence to the estimation of the relative populations of $^3$BDP and $^3$Por states and thus to the projected energy of $^3$BDP.

Figure 9:
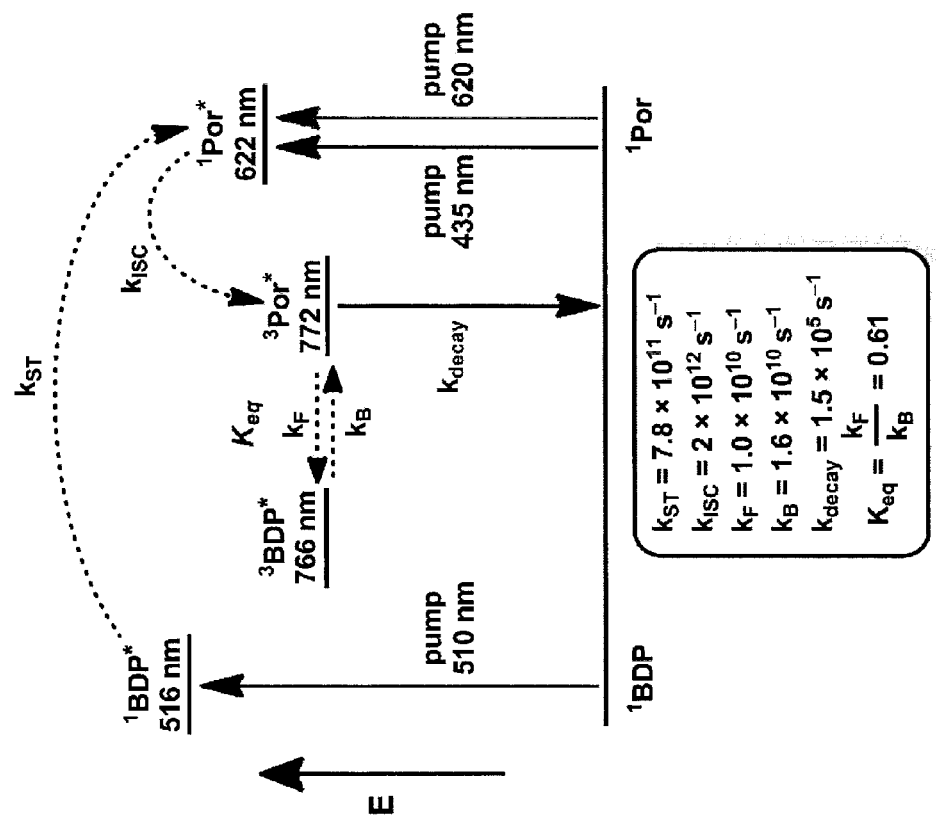
FIG. 9. is a Jablonski diagram summarizing the excited-state behavior of Pt(BDPTPBP) (4) upon selective irradiation of the BODIPY or benzoporphyrin units.

The combination of femtosecond and nanosecond TA studies with steady-state experiments allows construction of a Jablonski diagram describing the excited-state behavior of Pt($^{BDP}$TPBP) (4) (FIG. 9). After irradiation of the BODIPY fragment forms $^1$BDP*, fast singlet energy transfer generates an excited state on the platinabenzoporphyrin, $^1$Por*. Fast intersystem crossing to $^3$Por and overlap with the photobleach of the BODIPY unit render this state invisible to our transient absorption experiments. However, the energy of this state is known precisely due to the observation of extremely weak (φ<0.001) fluorescent emission at 628 nm mentioned above. Following intersystem crossing to $^3$Por, equilibration occurs between this state and the close-lying $^3$BDP, an efficient core-to-shell redistribution of excitation energy via TT. Since the lifetime of the $^3$BDP state greatly exceeds that of $^3$Por for 4, the decay of this equilibrated state is governed by the relative energies of these states (and consequently their relative populations) as well as the lifetime of $^3$Por.

Consequences of Using Multichromophoric Arrays for Triplet Generation

The efficient energy cascade depicted in FIG. 6 renders complex 4 analogous to the "cascatelles" developed by Ulrich, Ziessel, and co-workers, which are used to increase the apparent Stokes shifts of BODIPY fluorophores. In the present case, the combination of intense panchromatic absorption with bidirectional intramolecular singlet and triplet energy transfer makes the resulting phosphorescent cascatelle a unique example of a core-shell chromophore capable of efficiently tunneling energy to the core followed by redistribution back onto the antennae. This unusual set of interactions is made possible by the different singlet-triplet gaps associated with the BODIPY and benzoporphyrin moieties, which allow the behavior of this lowest-energy molecular excited state to be tuned without disturbing the complementary ground-state absorption properties of the ensemble.

As mentioned above, neat films of 4 only exhibit excimer emission at 77 K, indicating an energy loss pathway for this particular molecule that renders it less desirable as a donor for lamellar solar cells. Without wishing to be bound by theory, the findings reported herein show that modest tuning of the singlet-triplet gap for one of the units may disfavor this sort of deactivation.

EXAMPLES

Femtosecond Transient Absorption Spectroscopy

Femtosecond transient absorption measurements were performed using the output of a Ti:sapphire regenerative amplifier (Coherent Legend, 4 mJ, 35 fs) operating at a 1 kHz repetition rate. ~10% of the amplifier output was used to pump a type II OPA (Spectra Physics OPA-800C) and sum frequency of the signal and residual 800 nm pump generated 3.5 μJ excitation pulses centered at 508 nm with 6.5 nm of bandwidth. Prior to the sample, the excitation pulses were attenuated by a neutral density filter and were focused behind the sample using a 50 cm CaF$_2$ lens. Assuming a Gaussian profile, the pump spot size at the sample had a FWHM of 380 μm. Probe pulses were generated by focusing a small amount of the amplifier output into a rotating CaF$_2$ plate, yielding a supercontinuum spanning the range of 320-950 nm. A pair of off-axis aluminum parabolic mirrors collimated the supercontinuum probe and focused it into the sample.

The sample consisting of Pt($^{BDP}$TPBP) (4) dissolved in toluene solution was held in a 1 cm pathlength quartz cuvette under a deoxygenated atmosphere and had a peak optical density of 0.17 at 517 nm. The polarization of the pump and probe were set perpendicular to one another, which allowed for the suppression of scatter by passing the probe light transmitted by the sample through a polarizer prior to detection. A spectrograph (Oriel MS1271) was used to disperse the supercontinuum probe onto a 256 pixel silicon diode array (Hamamatsu), allowing multiplex detection of the transmitted probe as a function of wavelength. Pump induced changes in the probe were determined by using an optical chopper to block every other pump pulse. At early time delays, a strong nonresonant signal from the sample cell and solvent is observed and relaxes within 300 fs. Careful measurement of this nonresonant signal allowed for its partial subtraction from the transient data and also allowed the data to be corrected for temporal dispersion of the supercontinuum probe caused by propagation through the CaF$_2$ plate and sample.

The data presented were measured for a pump fluence of 150 μJ/cm$^2$. Based on the measured absorption cross section of Pt($^{BDP}$TPBP), at this fluence at most only a single excitation per Pt($^{BDP}$TPBP) molecule was expected. However, to verify that annihilation processes do not contribute to the signal, transient spectra was also measured using a pump fluence of 75 μJ/cm$^2$ and it was found that the signal scaled linearly between the two data sets.

Scheme 1. Synthesis of metalloporphyrin-based multichromophoric arrays.

a)

b)

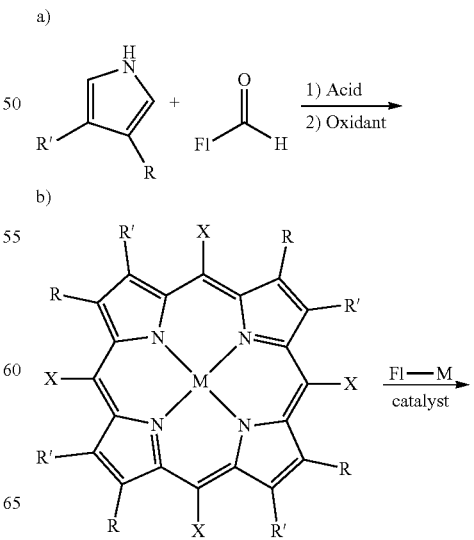

19
-continued
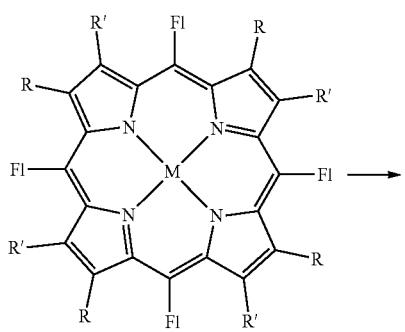
20
-continued
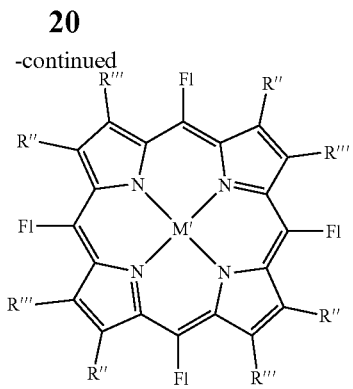
Example
Pt($^{BDP}$TPBP)
Scheme 2. Synthesis of Pt($^{BDP}$TPBP) (3).
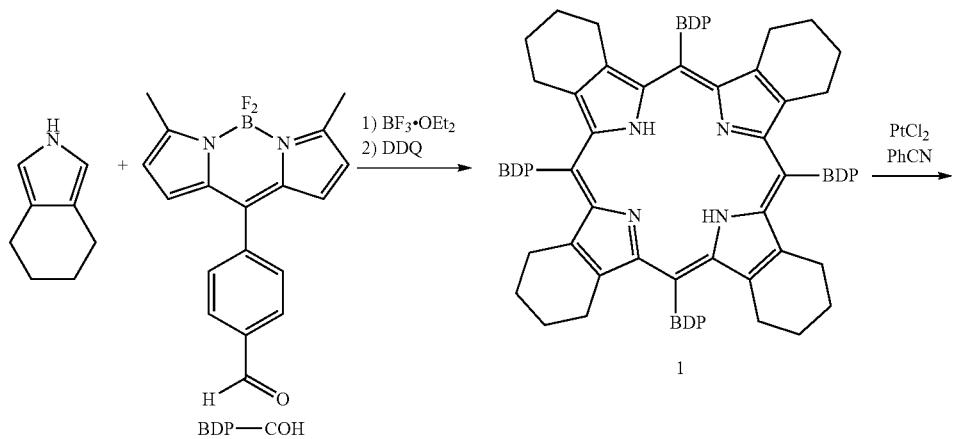
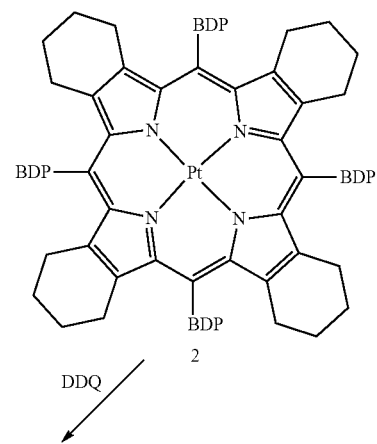

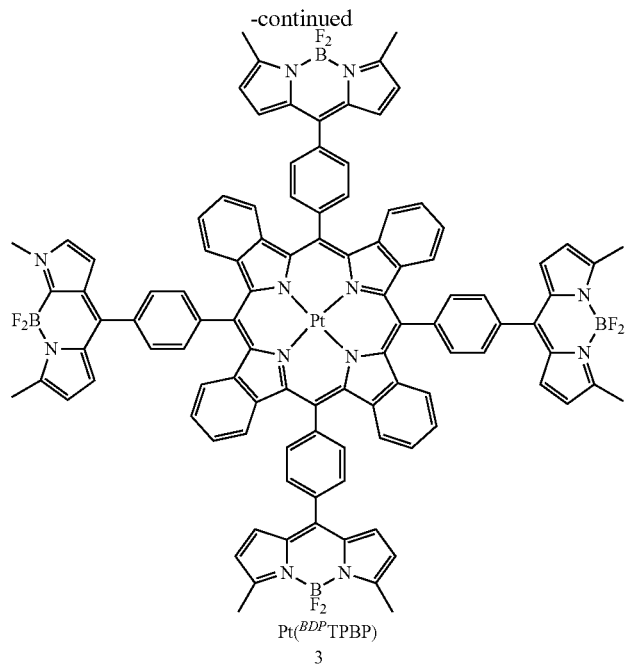

Pt(^{BDP}TPBP)
3

Cyclohexeneoporphyrin 1.(HCl)$_2$[H$_a$($^{BDP}$TPCHP)Cl$_2$]

Figure 13:
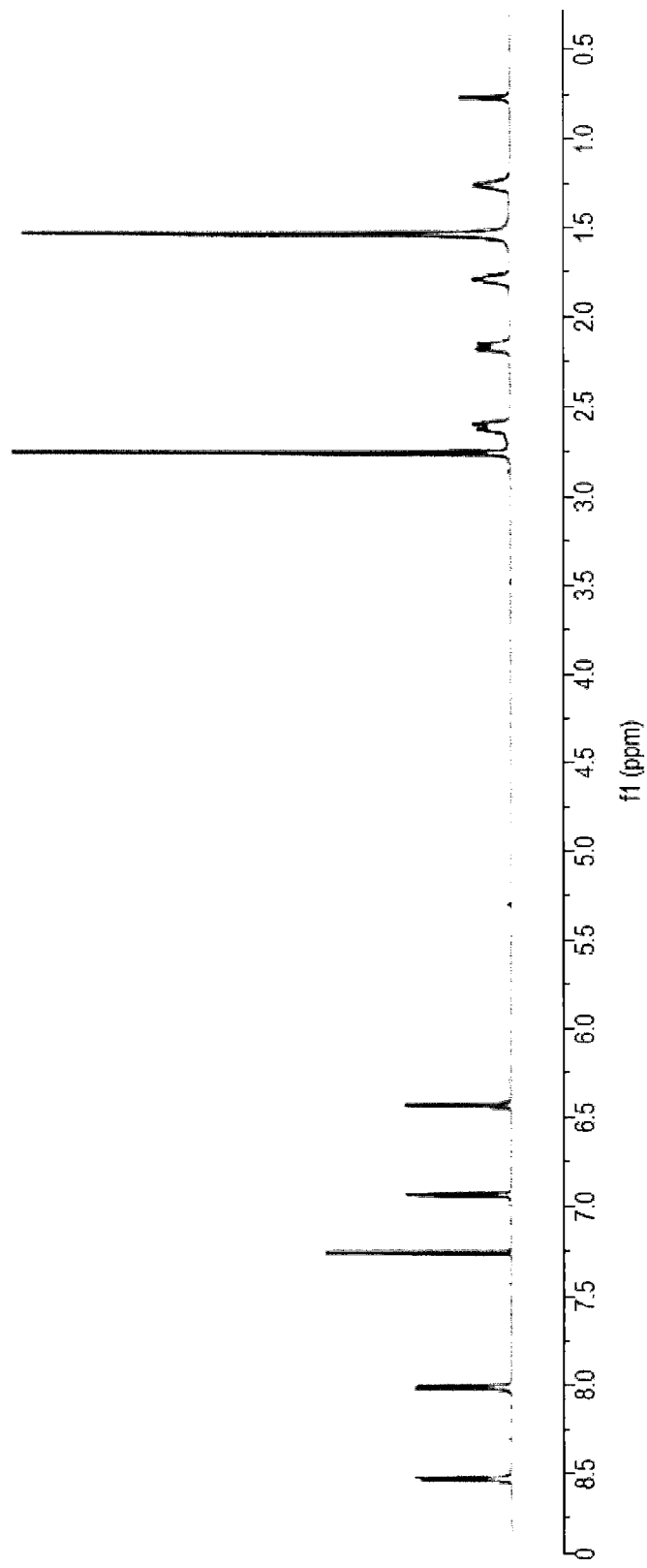
FIG. 13 is a diagram showing the $^1$H NMR spectra of cyclohexenoporphyrin 1.(HCl)$_2$[H$_4$($^{BDP}$TPCHP)Cl$_2$].

In a 3-neck roundbottom flask, dichloromethane (125 mL) was purged with N$_2$ with stirring for 20 min. The flask was shielded from light and 4,5,6,7-tetrahydroisoindole (54 mg, 0.45 mmol) and aldehyde BDP-COH (157 mg, 0.48 mmol) were added as solids, and the solution was stirred under N$_2$ for 10 min. BF$_3$.OEt$_2$ (20 μL, 0.10 mmol) was added via syringe and the resulting mixture was stirred for 2.5 h. DDQ (127 mg, 0.56 mmol) was added in one portion and the reaction was allowed to proceed with stirring for 18 h. The resulting red-brown solution was washed with 10% aq. Na$_2$SO$_3$ (3×50 mL) and brine (1×75 mL), dried (MgSO$_4$), filtered, and concentrated in vacuo to a brown film. These residues were purified by column chromatography on silica gel, first eluting with copious CH$_2$Cl$_2$ to remove residual fluorescent BODIPY impurities. After all BODIPY impurities had eluted (as judged by UV-vis spectroscopy), the desired product was eluted as a dark brown solution using CH$_2$Cl$_2$/THF (20:1), characterized by optical transitions at 347 nm (BODIPY), 435 and 483 nm (Soret peaks), 512 nm (BODIPY), 611 and 678 nm (Q bands). The free-base porphyrin was converted to the dication by washing with 5% aq. HCl (2×50 mL) and water (1×75 mL). The organics were dried (MgSO$_4$), filtered, and concentrated by rotary evaporation to a brown film. Porphyrin 2 was obtained in pure form as the green-brown bis(hydrochloride) salt by precipitation from CH$_2$Cl$_2$ upon layering with Et$_2$O (76 mg, 35%). UV-vis (CH$_2$Cl$_2$) $\lambda_{max}$ (log ε): 354 (4.6), 481 (5.3), 513 (5.2), 623 (3.9), 680 (4.3). $^1$H NMR (CDCl$_3$) (shown in FIG. 13): δ 8.54 (d, $^3J_{HH}$=8 Hz, 8H, phenyl Ar—H), 8.02 (d, $^3J_{HH}$=8 Hz, 8H, phenyl Ar—H), 6.94 (d, $^3J_{HH}$=4 Hz, 8H, BODIPY Ar—H), 6.44 (d, $^3J_HH$=4 Hz, 8H, BODIPY Ar—H), 2.77 (s, 24H, BODIPY —CH$_3$), 2.62 (dt, $^2J_{HH}$=17 Hz, $^3J_{HH}$=6 Hz, 8H, —CH$_2$), 2.16 (dt, $^2J_{HH}$=17 Hz, $^3J_{HH}$=6 Hz, 8H, —CH$_2$), 1.80 (m, 8H, —CH$_2$), 1.26 (m, 8H, —CH$_2$), 0.86 (s, 4H, —NH). MALDI, m/z for C$_{104}$H$_{90}$B$_4$F$_8$N$_{12}$ calcd 1703.8, found 1702.1.

Platinum Cyclohexenoporphyrin 2 [Pt($^{BDP}$TPCHP)]

Figure 14:
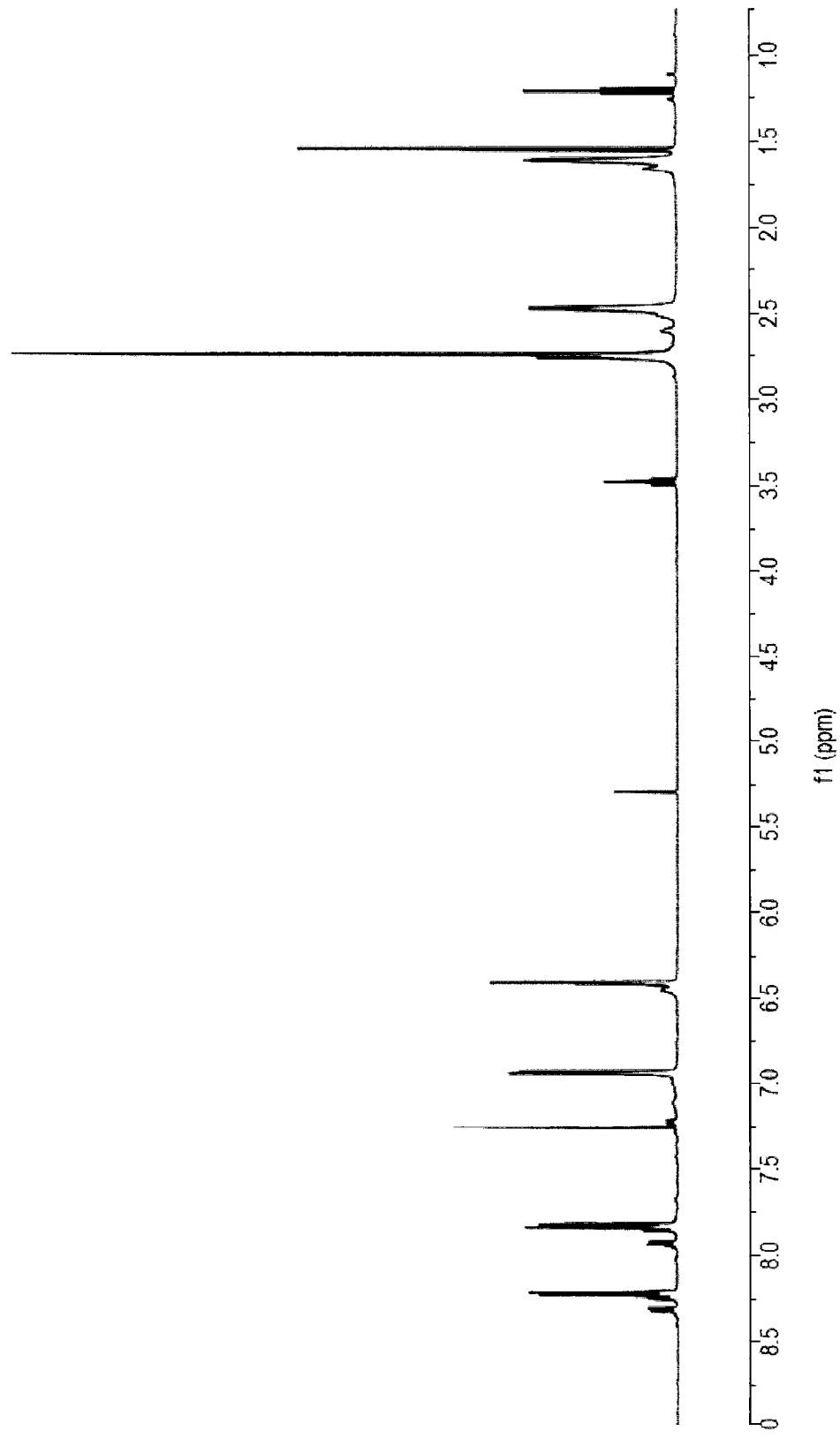
FIG. 14 is a diagram showing the $^1$H NMR spectra of platinum cyclohexenoporphyrin 2 [Pt($^{BDP}$TPCHP)].

Platinum(II) chloride (40 mg, 0.15 mmol) was added to dry, degassed benzonitrile (40 mL), and the mixture was heated with stirring under N$_2$ at 100° C., causing the platinum salts to dissolve as the solution turned yellow. The cyclohexenoporphyrin dication 1.(HCl)$_2$ (40 mg, 0.023 mmol) was added as a solid, and the resulting solution was heated with stirring at reflux for 3 h. The mixture was cooled to ambient temperature and benzonitrile removed by vacuum distillation. The residues were dissolved in CH$_2$Cl$_2$ and filtered to remove solids, and the filtrated was dried in vacuo to afford a dark brown powder, which was further purified by washing with methanol (3×10 mL). The powder was subjected to column chromatography (SiO$_2$ gel, CH$_2$Cl$_2$ efluent), and the cleanest fractions combined, dried by rotary evaporation, and crystallized as green plates by layering a concentrated solution of 3 in CH$_2$Cl$_2$ with Et$_2$O. UV-vis (CH$_2$Cl$_2$) $\lambda_{max}$ (log ε): 340 (4.8), 410 (5.4), 512 (5.5), 569, (4.4). $^1$H NMR (CDCl$_3$) (shown in FIG. 14): δ8.22 (d, J=8 Hz, 8H, phenyl Ar—H), 7.83 (d, J=8 Hz, 8H, phenyl Ar—H), 6.94 (d, J=4 Hz, 8H, BODIPY Ar—H), 6.41 (d, J=4 Hz, 8H, BODIPY Ar—H), 2.75 (s, 24H, —CH$_3$), 2.48 (s, 16H, —CH$_2$), 1.61 (s, 16H, —CH$_2$).

Platinum Benzoporphyrin 3 [Pt($^{BDP}$TPBP)]

Figure 15:
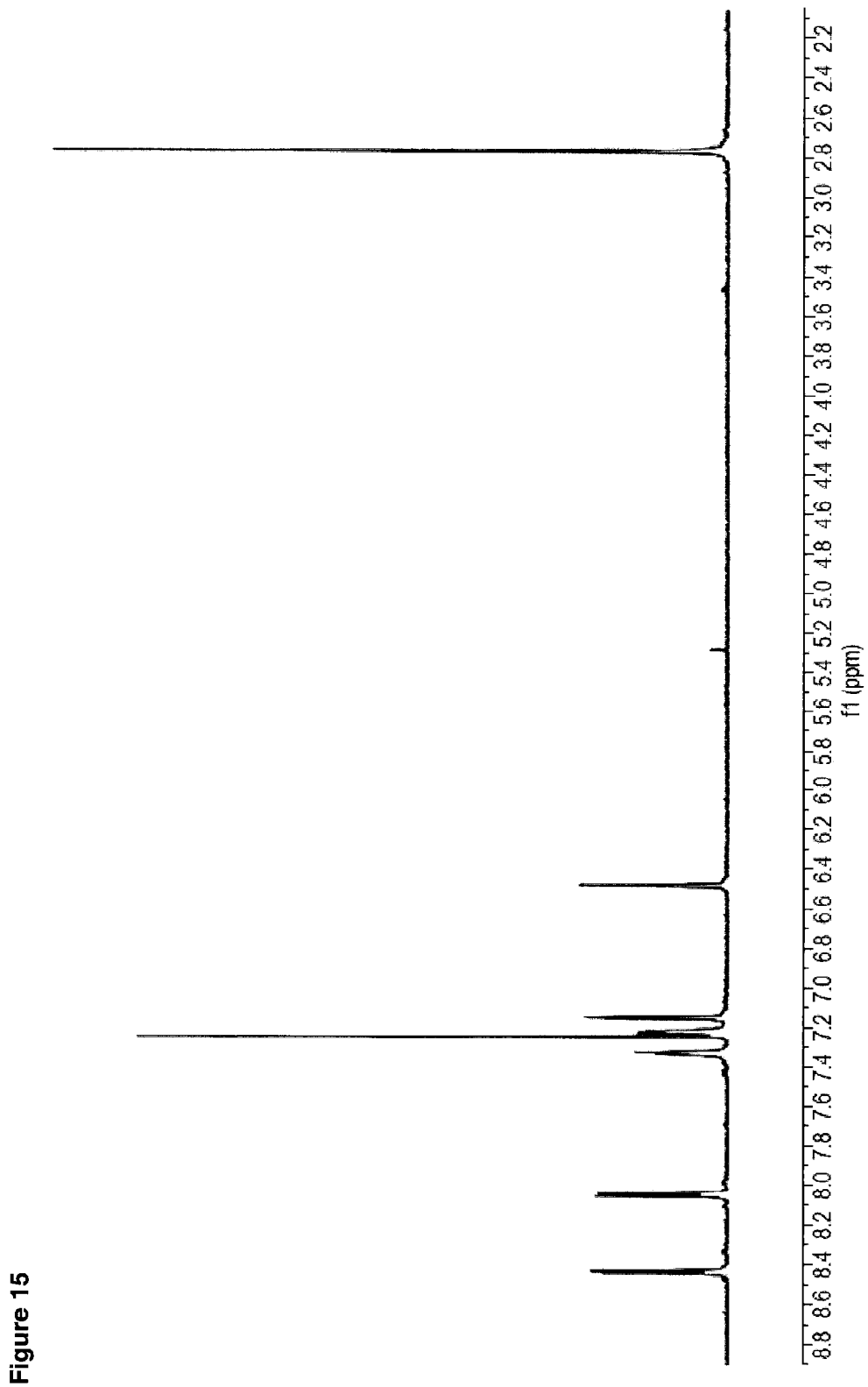
FIG. 15 is a diagram showing the $^1$H NMR spectra of platinum benzoporphyrin 3 [Pt($^{BDP}$TPBP)].

Platinum cyclohexenoporphyrin 2 (Pt($^{BDP}$TPCHP), 33 mg, 0.017 mmol) was dissolved in toluene (30 mL). DDQ (40 mg, 0.18 mmol) was added and the solution was heated at reflux with stirring for 1.5 h, causing the color to change from brown to olive. The resulting solution was washed with sodium sulfite (10% aq, 2×50 mL) and brine (1×50 mL), dried (MgSO$_4$), filtered and concentrated in vacuo to a dark solid. These dark residues were dissolved in minimal CH$_2$Cl$_2$ (ca. 1 mL) and the solution layered with Et$_2$O, causing black solids to precipitate overnight. The compound was purified by an additional precipitation from CH$_2$Cl$_2$ with Et$_2$O, yielding the title compound as a black solid that was isolated by filtration. UV-vis (CH$_2$Cl$_2$) $\lambda_{max}$ (log ϵ): 281 (4.98), 340 (4.83), 433 (5.40), 514 (5.48), 573 (4.34), 619 (5.07). $^1$H NMR (CDCl$_3$) (shown in FIG. 15): δ 8.45 (d, J=8 Hz, 8H, phenyl Ar—H), 8.06 (d, J=8 Hz, 8H, phenyl Ar—H), 7.33-7.36 (m, 8H, porphyrin Ar—H), 7.24-7.26 (m, 8H, porphyrin Ar—H), 7.16 (d, J=4 Hz, 8H, BODIPY Ar—H), 6.50 (d, J=4 Hz, 8H, BODIPY Ar—H), 2.79 (s, 24H, —CH$_3$).

Characterization of Pt($^{BDP}$TPBP) and Demonstration of Efficient Triplet Harvesting Complex 3 has been thoroughly characterized by photophysical studies, summarized below, which highlight the primary claimed benefits of attaching multiple appropriate fluorophores antennae to porphyrins: 1) increased absorption across visible wavelengths; 2) efficient antenna→porphyrin energy transfer, indicating that efficient light harvesting is possible; 3) efficient generation of triplets from excited states generated on the antennae and porphyrin core, leading to red-shifted (often near-infrared (NIR)) emission upon photoexcitation at a wide range of wavelengths.

Figure 10:
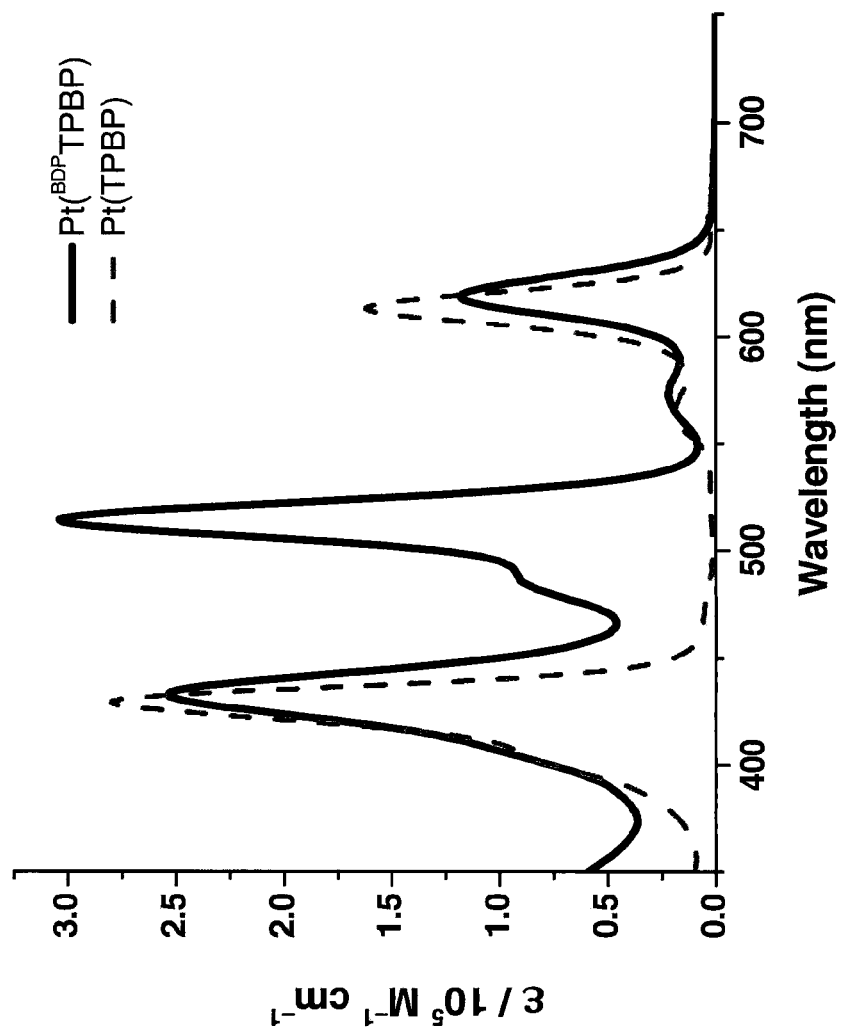
FIG. 10. is a diagram showing absorption spectrum of Pt(BDPTPBP) (3, black line) in CH$_2$Cl$_2$ at ambient temperature compared with the parent Pt(TPBP) complex with no antennae (green dash).
Figure 11:
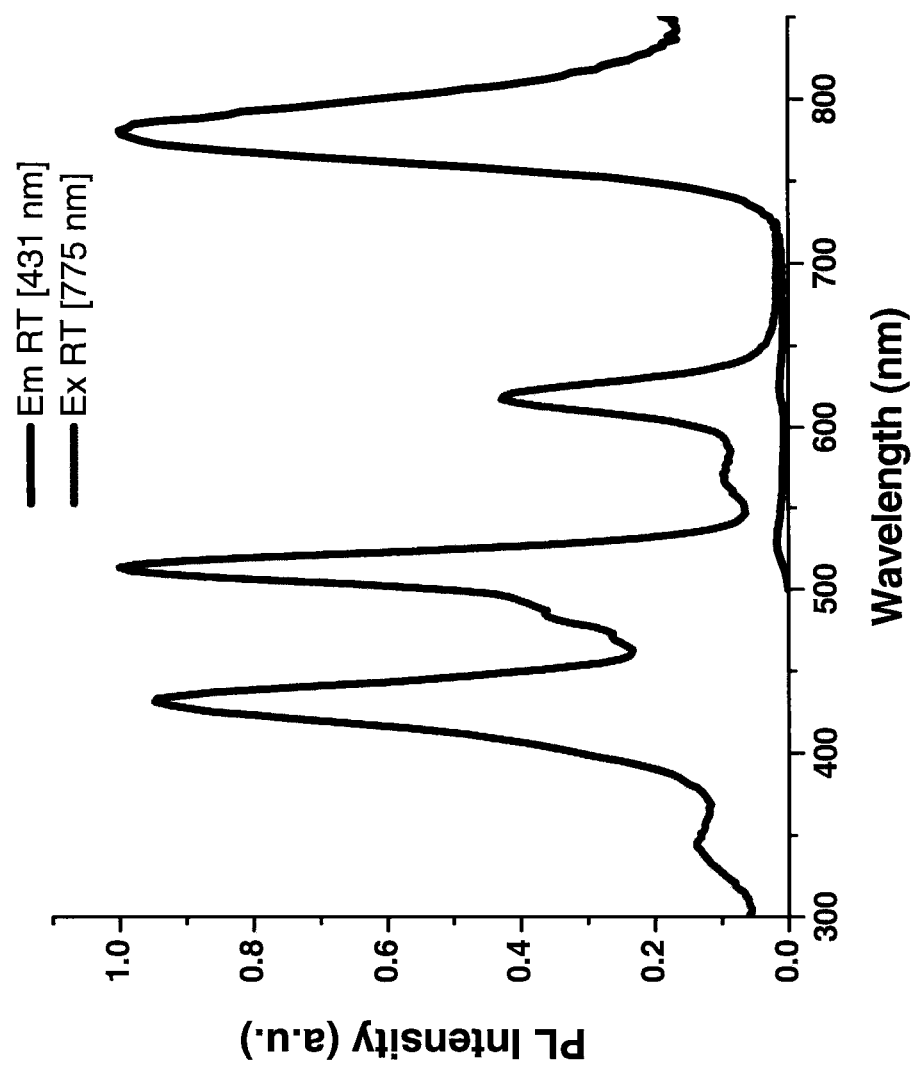
FIG. 11. is a diagram showing excitation ($\lambda_{em}$=775 nm) and emission ($\lambda_{em}$=431 nm) spectra of 3 at room temperature in CH$_2$Cl$_2$.

As shown in FIG. 10, the addition of 4 BODIPY antennae to the benzoporphyrin core gives a significant increase in the absorption of 3 from 450-550 nm relative to the parent Pt(TPBP) complex with no antennae. This complex exhibits photoluminescence (PL) with a single primary emission at 770 nm (FIG. 11). PL efficiencies are high in rigid media, reaching 17% when 3 is doped into a poly(methyl methacrylate) (PMMA) thin film (0.5%).

Figure 12:
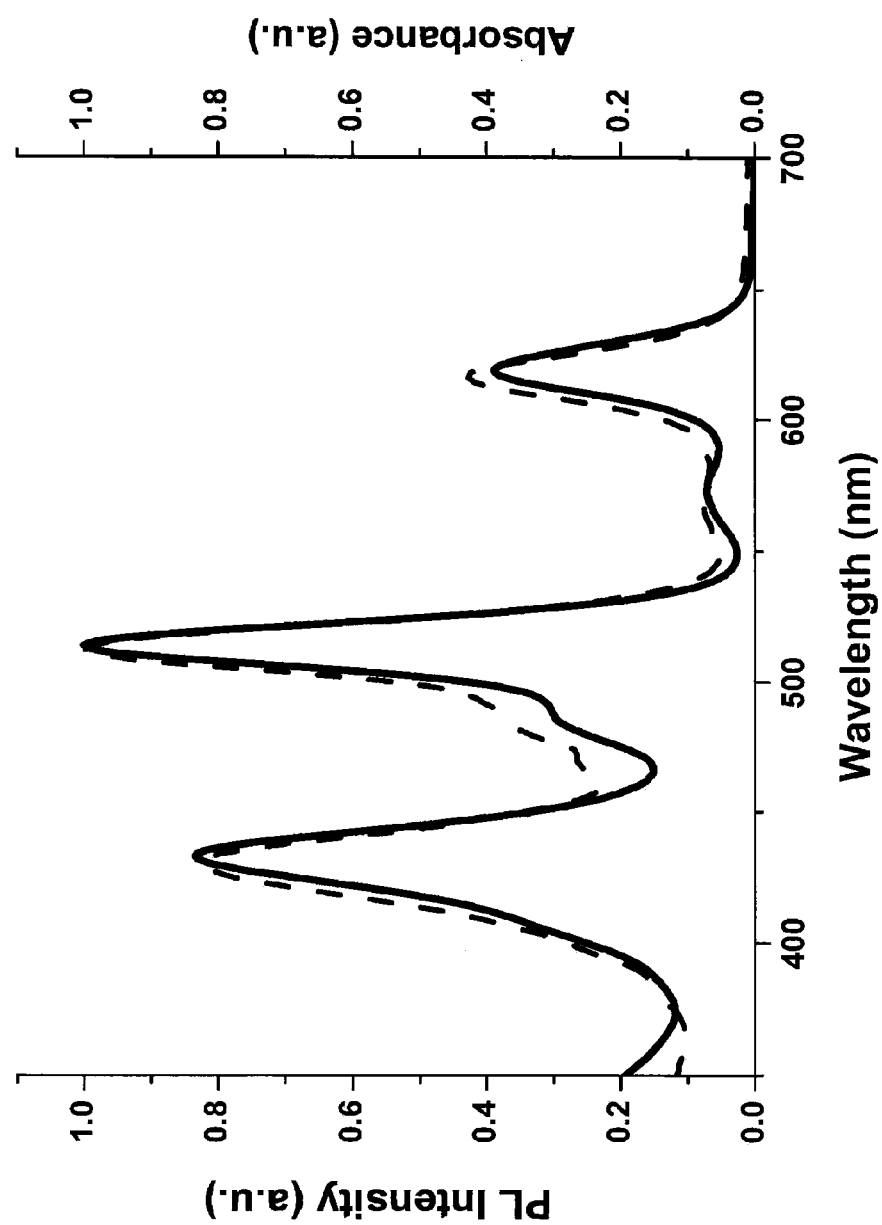
FIG. 12. is a diagram showing a comparison of excitation spectrum of 3 in PMMA (0.5%) (dashed, $\lambda_{em}$=768 nm) with absorption of 3 in CH$_2$Cl$_2$ at ambient temperature (solid line), confirming complete BODIPY→porphyrin energy transfer.

A comparison between absorption and excitation spectra, normalized to the Soret, of the peak intensities at 512 nm, where the BODIPY antennae are the only significant absorbers, shows that BODIPY→porphyrin energy transfer is quantitative in rigid media such as a doped PMMA film (ambient temperature) or 2-methyltetrahydrofuran glass (77K) (FIG. 12). Additionally, BODIPY→porphyrin energy transfer is quite efficient in dilute CH$_2$Cl$_2$ solution at ambient temperature ($\phi_{EnT}$=90%). Since this efficient energy transfer leads to platinum porphyrin phosphorescence, it is clear that the singlet excited states generated at the antennae are cleanly funneled to triplet platinum porphyrin-based excitons, a phenomenon that may prove quite useful in solar cells and imaging applications.

Unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A multichromophoric assembly comprising a metalloporphyrin of Formula I

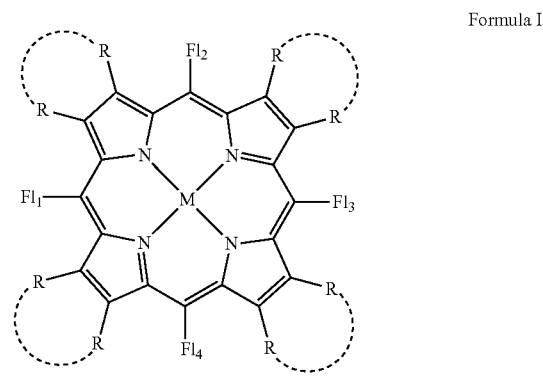

Formula I or salts or tautomers thereof, wherein:
Fl$_1$, Fl$_2$, Fl$_3$ and Fl$_4$ are each independently selected from the group consisting of 4,4-difluoro-4-bora-3a,4a-diaza-s-indacene, fluorescein, and merocyanine-based dyes, wherein the Fl$_1$, Fl$_2$, Fl$_3$, and Fl$_4$ are directly attached to the metalloporphyrin scaffold or are attached via a linker chosen from alkyl and phenylene;
R is selected from the group consisting of hydrogen, optionally substituted alkyl, optionally substituted aryl, optionally substituted heteroalkyl, and optionally substituted heteroaryl; or
one or more R groups may be connected to form a cycloalkyl or benzannulated ring system; and
M is selected from the group consisting of Y, La, Zr, Hf, Nb, Ta, Mo, W, Tc, Re, Ru, Os, Rh, Ir, Pd, Pt, Ag, Au, Cd, Hg, Ga, Ge, In, Sn, Sb, Ti, Pb, and Bi, which can be optionally bound to one or more additional neutral or anionic ligands, wherein the ligands are selected from the group consisting of pyridine, imidazole, pyrazine, furan, thiophene, halides, sulfonates and caboxylates.

2. The multichromophoric assembly according to claim 1, wherein the sulfonates are trifluoromethanesulfonate groups and the carboxylates are acetate groups.

3. The multichromophoric assembly according to claim 1, wherein adjacent R groups are connected to form a cyclohexene ring, benzene ring, or combination thereof.

4. The multichromophoric assembly according to claim 1, wherein the cycloalkyl or benzannulated ring system comprise porphyrins.

5. The multichromophoric assembly according to claim 4, wherein the porphyrins comprise benzoporphyrins, naphthoporphyrins, and anthracenoporphyrins.

6. The multichromophoric assembly according to claim 1, wherein the metalloporphyrin of Formula I is

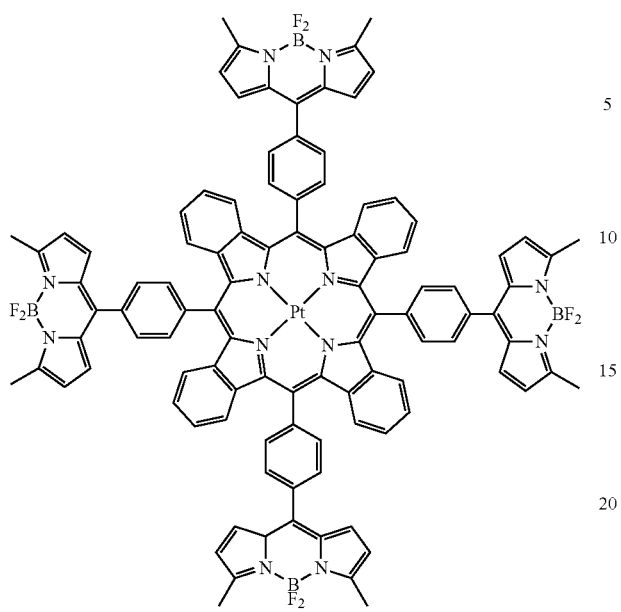

or salts or tautomers thereof.

7. The multichromophoric assembly according to claim 1, further comprising at least one triplet forming dopant material.

8. The multichromophoric assembly according to claim 1, wherein the $Fl_1$, $Fl_2$, $Fl_3$, and $Fl_4$ exhibit a) strong absorption either at higher energy than the porphyrin Soret or at intermediate energy between the porphyrin Soret and Q band(s); or b) efficient transfer of energy from the photoexcited state to the metalloporphyrin scaffold core.

9. The multichromophoric assembly according to claim 1, wherein M facilitates intersystem crossing such that photons absorbed by the $Fl_1$, $Fl_2$, $Fl_3$, and $Fl_4$ are efficiently funneled to a porphryin-based triplet state.

10. The multichromophoric assembly according to claim 1, comprising one platinum tetraphenyltetrabenzoporphyrin (Pt(TPBP)) core and four dimethyl boron dipyrrin $Me_2BODIPY$ moieties forming a shell in a core-shell arrangement, which exhibits energy transfer properties sufficient to funnel singlet to the core followed by triplet redistribution between the core and shell.

11. The multichromophoric assembly according to claim 1, wherein there is energy transfer between at least one of the $Fl_1$, $Fl_2$, $Fl_3$ and $Fl_4$ and the metalloporphyrin, or any combination thereof.

12. The multichromophoric assembly according to claim 11, wherein the energy transfer occurs via Förster resonant energy transfer (FRET).

13. A method for generating electric-field-stabilized geminate polaron pairs, comprising applying an electric field to a metalloporphyrin of Formula I

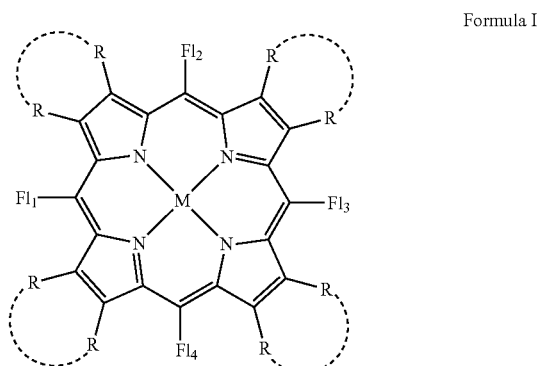

Formula I or salts or tautomers thereof, wherein:

$Fl_1$, $Fl_2$, $Fl_3$ and $Fl_4$ are each independently selected from the group consisting of 4,4-difluoro-4-bora-3a,4a-diaza-s-indacene, fluorescein, and merocyanine-based dyes, wherein the $Fl_1$, $Fl_2$, $Fl_3$, and $Fl_4$ are directly attached to the metalloporphyrin scaffold or are attached via a linker chosen from alkyl and phenylene;

R is selected from the group consisting of hydrogen, optionally substituted alkyl, optionally substituted aryl, optionally substituted heteroalkyl, and optionally substituted heteroaryl; or one or more R groups may by connected to form a cycloalkyl or benzannulated ring system; and M is selected from the group consisting of Y, La, Zr, Hf, Nb, Ta, Mo, W, Tc, Re, Ru, Os, Rh, Ir, Pd, Pt, Ag, Au, Cd, Hg, Ga, Ge, In, Sn, Sb, Ti, Pb, and Bi, which can be optionally bound to one or more additional neural or anionic ligands, wherein the ligands are selected from the group consisting of pyridine, imidazole, pyrazine, furan, thiophene, halides, sulfonates and caboxylates, and wherein charge separation to form geminate pairs are achieved without external dopants.

* * * * *